United States Patent [19]
Bustos et al.

[11] Patent Number: 6,160,202
[45] Date of Patent: Dec. 12, 2000

[54] MODIFICATION OF SEED CROPS WITH TRANSCRIPTION FACTORS

[75] Inventors: Mauricio M. Bustos, Catonsville; Maw-Shenq Chern, Baltimore, both of Md.

[73] Assignee: University of Maryland Baltimore County, Baltimore, Md.

[21] Appl. No.: 08/796,899

[22] Filed: Feb. 6, 1997

Related U.S. Application Data

[63] Continuation of application No. 08/319,544, Oct. 7, 1994, abandoned.

[51] Int. Cl.[7] .......................... C12N 15/29; C12N 15/82; A01H 5/00
[52] U.S. Cl. ....................... 800/278; 800/281; 800/312; 800/313; 435/69.1; 435/320.1; 435/468; 536/23.6; 536/24.1
[58] Field of Search .................................. 536/23.6, 24.1; 435/69.1, 172.3, 320.1, 468; 800/205, 278, 281, 298, 312, 313

[56] References Cited

U.S. PATENT DOCUMENTS 5,362,864   11/1994   Chua ...................................... 536/23.6

OTHER PUBLICATIONS

Bobb et al. Plant J. 8(3): 331–343.
Smith et al. 1988. Nature 334: 724–726.
Napoli et al. 1990. Plant Cell 2: 279–289.
Erlich et al. 1992. Gene 117(2): 169–178.
Bustos et al. 1989. Plant Cell 1(9): 839–853.
Bustos et al. 1991. EMBO J 10(6): 1469–1479.

*Primary Examiner*—David T. Fox
*Attorney, Agent, or Firm*—Burns, Doane, Swecker & Mathis, L.L.P.

[57] ABSTRACT

The present invention relates to an isolated transcription factor gene which is expressed in a maturing dicot seed and which encodes a transcription factor protein which targets a promoter of a gene encoding seed storage proteins. One group of such genes binds to 7S globulin (b-phaseolin) or lectin (PHA-L) promoters. Transcription factors identified as Pv Seed Factor-1 (PvSF1) and Vicilin-box Binding Protein-1 (VBP1) have been isolated.

There is also disclosed a method for enhancing or reducing expression of seed storage protein, lectin or oil-protein genes in dicot seed crops comprising transforming a seed crop plant with the transcription factor gene of the invention.

16 Claims, 44 Drawing Sheets

Fig. 1a

```
bZIP1 5'race clone 507
top strand
bz1a507.seq  Length: 1546    12:33    Type: N    Check: 6172    ..

1  AATTTGTGTT TCACATTCCA ACTAGCGTGC GCTGGTACAA TCCACCGTGC
  51  CCACACCTCA CCCTTCTCCT TTTCTCTTTC GAGTTTCCAA CGCAACAACA
 101  GCCACAGGAG TTGTTGAAAA TAACAAACAA ACATTTACTG TTACCCTCCT
 151  ACCTTCTCAG ACGCACGCCA CAACAACCAC CTTCTCAGAC ACAACACTAA
 201  CAAACGTTTC TTTGCAACAC TCTTCAGTTT CAGTTTTCCC ATGATACAAT
 251  TATAGCTACA TCAAACCAAA AGCCTAGTGT CGAATTATTG ACTTCAAATT
 301  TTAAATCCAC TTTGTCCCAT CCCACCCTGGA CTTCCACCTC ATCCTTCTTC
 351  TCAACGCCAT GAAAATAGTG TGTGTTTTCT GACAGGAATC TATTCAACTA
 401  GATCTTCTGA CCTCCATAGA TATCAGCACT TGATCATAGG TCTTTTTTGT
 451  TTCTGTGGCT GAGAGGAAGT GATTCTAAAC TAATCTATAT GGGGGCTGGG
 501  GAAGAGAGCA CAACAAAATC TTCCAAGTCA TCTTCATCAG TTCAGGAGAC
 551  ACCAACAGTG CCTGCATATC CTGATTGGTC AAGCTCCATG CAGGCCTATT
 601  ATGCTCCTGG AGCTGCTCCA CCTCCCTTTT TTGCCTCAAC TGTTGCATCC
 651  CCAACTCCCC ATCCCTATTT ATGGGGAAGC CAGCATCCTT TGATGCCACC
 701  ATATGGGACT CCTGTCCCAT ATCCAGCTTT ATATCCTCCT GGGAGTATCT
```

Fig. 1b

```
 751  ATGCTCATCA TCCAAGCATG GCAGTGACTC CGAGTGTTGT CCAGCAAAGT
 801  ACGGAGATTG AAGGGAAGGG AACTGATGGA AAGGATCGAG ACTCGTCCAA
 851  AAAATTGAAA GGAACTTCTG CAAATGCAGG TTCCAAAGCA GGAGAGAGTG
 901  GAAAGGCAGG CTCAGGTTCA GGCAATGATG GCATGTCTCA AAGTGGTGAA
 951  AGTGGTTCAG AGGGTTCATC GAATGCTAGT GATGAGAATA ATAACCAACA
1001  GGAATCAGCT ACAAACAAGA AGGGAAGCTT TGACCTGATG CTTGTTGATG
1051  GAGCCAATGC CCAGAACAAT TCTGGGGGTG CCATTTCTCA ATCTTCTATG
1101  CCTGGGAAGC CTGTTGTCTC AATGCCAGCA ACTAATCTTA ATATTGGAAT
1151  GGACTTATGG AATGCATCAT CCGGTGGTGG CGAAGCTGCA AAAATGAGAC
1201  ATAATCAATC TGGTGCCCCA GGAGTTGTTG CCCTTGGTGA ACAATGGATA
1251  CAAGATGAAC GTGAGCTGAA AAGACAGAAG AGAAAACAGT CAAACAGAGA
1301  CTCAGCTAGG AGGTCAAGGT TACGCAAGCA GGCTGAGTGC GAAGACTTAC
1351  AAAAGAGGGT GGAGACACTG GGAAGTGAGA ATCGAACACT CAGAGAAGAG
1401  CTTCAGAGAC TTTCCGAAGA ATGCGAGAAG CTTACATCTG AAAATAGTTC
1451  AATCAAGGAA GAATTGGAAC GGATGTGTGG GCCAGAAGCA GTTGCTAACC
1501  TTGGATGACA CAAAACATTT GAGTTCCTCA GTGTAGTGTT TGATGG
```

Fig. 1c (Linear) MAP of: bzla507.seq check: 6172 from: 1 to: 1546 bZIP1 5'race clone 507
top strand

With 191 enzymes: *

```
                    C         H    R     M
                    a         h    s     m
              B     c    H    a    a     e
              f     8    i    I    I     I
              a     I    n    I    I     I
              I     I    f    I    I     I         B
                                                   s
                                                   p
                                                   1
                                                   H2
                                                   p8
                                                   h6
                                                   II
    AATTTGTGTTTCACATTCCAACTAGCGTGCGCTGGTACAATCCACCGTGCCCACACCTCA
1   ------+---------+---------+---------+---------+---------+   60
    TTAAACACAAAGTGTAAGGTTGATCGCACGCGACCATGTTAGGTGGCACGGGTGTGGAGT a    N  L  C  F  F  Q  L  A  C  A  G  T  I  H  R  A  H  T  S  -
b    I  C  V  S  H  S  N  *  R  A  L  V  Q  S  T  V  P  P  H  -
c    F  V  F  H  I  P  T  S  V  R  W  Y  N  P  P  C  P  H  L  T -
```

Fig. 1d

```
              R                          T                    M      C
              Ml                         a                    w      v    M
              ne                         q                    o      i    m
              1A                         I                    I      J    e
              II                         I                    I      I    I
       CCCTTCTCCTTTTCTCTTTCGAGTTTCCAACGCAACAGCCACAGGAGTTGTTGAAAA     120
61     ------+---------+---------+---------+---------+---------+
       GGGAAGAGGAAAAGAGAAAGCTCAAGGTCGTTGTCGGTGTCCTCAACTTT
    a    P  F  S  F  L  S  S  F  Q  R  N  S  H  R  S  C  *  K
    b    P  S  P  F  L  F  R  V  S  N  A  T  A  T  G  V  V  E  N
    c    L  L  F  S  F  E  F  P  T  Q  Q  Q  P  Q  E  L  L  K  I

T  T
                           t  t
                           Mh h
                           al 1                        MD         C
                           el 1                        nd    H    a    H
                           II H                        le    a    c    g
                           II I                        II    I    I    I
       TAACAAACAAACATTTACTGTTACCCTCCTACCTTCTCAGACGCCACGCCACAACAACCAC    180
121    ------+---------+---------+---------+---------+---------+
       ATTGTTTGTTTGTAAATGACAATGGGAGGATGGAAGAGTCTGCGTGCGGTGTTGTTGGTG
    a    *  Q  T  N  I  Y  C  Y  P  P  T  F  S  D  A  R  H  N  N  H
    b    N  K  Q  T  F  T  V  T  L  L  P  S  Q  T  H  A  T  T  T
    c    T  N  K  H  L  L  P  S  Y  L  R  R  R  T  P  Q  Q  P  P a
b
c
```

Fig. 1e

```
         P                                                                           E
         s                                                                           a
         p          E                          M  C                                  r
         M1         c                          b  v                                  I
         a4         o                          o  i                                  I
         e0         5                          I  R                                  I
         I6         7                          I  I                                  I
         II         I                          I  I                                  /
     CTTCTCAGACACAACACTAACAAACGTTTCTTTGCAACACTCTTCAGTTTTCCC
181  -----+---------+---------+---------+---------+---------+  240
     GAAGAGTCTGTGTTGTTGATTGTTTGCAAAGAAACGTTGTGAGAAGTCAAAAGGG

L  L  R  H  N  T  N  K  R  F  F  A  T  L  F  S  F  S  F  P
    F  S  D  T  T  L  T  N  V  S  L  Q  H  S  S  V  F  Q  F  P
    S  Q  T  Q  H  *  Q  T  F  L  C  N  T  L  Q  F  S  V  S  H
a
b
c

T                                                 T
         N        s        C                      C        p  B     s        p  B
         1        p        A v                    v  B     A 5      p  0     A 5
         a        5        l i                    i  f     a  0     p  0     o  9
         H        0        i J                    J  a     q  9     o  9     I  I
         I        9        H I                    I  I     I  I     I  I     I  I
         I        I                                                          /
     ATGATACAATTATAGCTACATCAAAACCAAAAGCCTAGTGTCGAATTATTGACTTCAAATT
241  -----+---------+---------+---------+---------+---------+  300
     TACTATGTTAATATCGATGTAGTTTTGGTTTTCGGATCACAGCTTAATAACTGAAGTTTAA

TTAAATCCACTTTGTCCCATCCCACCTGGACTTCCACCTCATCCTTCTTCTCAACGCCAT
      301 ------+---------+---------+---------+---------+---------+ 360
         AATTTAGGTGAAACAGGGTAGGGTGGACCTGAAGGTGGAGTAGGAAGAAGAGTTGCGGTA a   L  N  P  L  C  P  I  P  P  G  L  P  P  H  P  S  S  Q  R  H  -
       b   *  I  H  F  V  P  S  H  L  D  F  H  L  I  L  L  N  A  M  -
       c       K  S  T  L  S  H  P  T  W  T  S  S  F  F  S  T  P  *  -

S
         N                H      M      BB a
         l              i T    X    B  g s Du
         a              n f    m    o  f l t p 3
         H              f i    n    I  a I Y n A
         I              I I    H    I  I I I I I
                          /               /

GAAAAATAGTGTGTGTGTTTCTGACAGGAATCTATTCAACTAGATCTTCTGACCTCCATAGA
      361 ------+---------+---------+---------+---------+---------+ 420
         CTTTTTATCACACACAAAGACTGTCCTTAGATAAGTTGATCTAGAAGACTGGAGGTATCT a   E  N  S  V  C  F  L  T  G  I  Y  S  T  R  S  S  D  L  H  R  -
       b   K  I  V  C  V  F  *  Q  E  S  I  Q  L  D  L  T  S  I  D  -
       c   K  *  C  V  F  S  D  R  N  L  F  N  *  I  F  *  P  P  I  -
```

Fig. 1g

```
                    S                          C                      H
                    a                          M vD                   Xi T
       E            BuD                        n id                   mn f
       cM           c3p                        l Je                   nfi
       on           1An                        I II                   III
       Rl           III
       VI
       /                                                              /
       TATCAGCACTTGATCATAGGTCTTTTTTGTTTCTGTGGCTGAGAGGAAGTGATTCTAAAC
421    ----+----+----+----+----+----+----+----+----+----+----+----+  480
       ATAGTCGTGAACTAGTATCCAGAAAAAACAAAGACACCGACTCTCCTTCACTAAGATTTG a   Y  Q  H  L  I  G  L  F  C  F  C  G  *  E  E  V  I  L  N  -
   b   I  S  T  *  S  *  V  F  F  V  S  V  A  E  R  K  *  F  *  T  -
   c   S  A  L  D  H  R  S  F  L  F  L  W  L  R  G  S  D  S  K  L  -

B
                            s
                            Ap                                B
                   C        11MM                  M           s  m
                   vE       w2bb                  b           m  A
                   ia       28oo                  o           A  I
                   Jr       16II                  I           I
                   II       IIII
                   /     //
       TAATCTATATGGGGGCTGGGGAAGAGAGCACAACAAAATCTTCCAAGTCATCTTCATCAG
481    ----+----+----+----+----+----+----+----+----+----+----+----+  540
       ATTAGATATACCCCCGACCCCTTCTCTCGTGTTGTTTTAGAAGGTTCAGTAGAAGTAGTC a   *  S  I  W  G  L  G  K  R  A  Q  Q  N  L  P  S  H  L  H  Q  -
   b   N  L  Y  G  G  W  G  R  E  H  N  K  I  F  Q  V  I  F  I  S  -
   c   I  Y  M  G  A  G  E  E  S  T  T  K  S  S  K  S  S  S  S  V  -
```

Fig. 1h

```
                                                    C             N         H
                    AC  C                           Av            ClC   C   a
                    la  v                           li            vaa vHeS BM
                    wc  i                           uJ            iIc iaIt bw
                    N8  R                           II            RI8 JeIu vo
                    II  I                                         III IIII II
                                                    /             /    /    ///
541  TTCAGGAGACACCAACAGTGCCTGCATATCCTGATTGGTCAAGCTCCATGCAGGCCTATT
     ----+----|----+----|----+----|----+----|----+----|----+----  600
     AAGTCCTCTGTGGTTGTCACGGACGTATAGGACTAACCAGTTCGAGGTACGTCCGGATAA F  R  R  H  Q  Q  C  L  H  I  L  I  G  Q  A  P  C  R  P  I  -
     S  G  D  T  N  S  A  C  I  S  *  L  V  K  L  H  A  G  L  L  -
     Q  E  T  P  T  V  P  A  Y  P  D  W  S  S  M  Q  A  Y  -

E        C
           c  S     C      B  MF                   C        S
           o  c  M  AvI    p  no                   MvF      f     B
           R  r  w  lit    m  lk                   nio      a     c
           I  F  o  uJa    I  II                   lRk      N     c
           I  I  I  III                            III      I     I
              //

601  ATGCTCCTGGAGCTGCTCCACCTCCCTTTTTGCCTCAACTGTTGCATCCCCAACTCCCC
     ----+----|----+----|----+----|----+----|----+----|----+----  660
     TACCGAGGACCTCGACGAGGTGGAGGGAAAAACGGAGTTGACAACGTAGGGGTTGAGGGG

```
                    C  CS       S       B    P     S NBfP  P    H  P      B
                 BF v  af       f       s    NBfP  m dsll  s    h  s      m
                 so i  ca       a         F  elMe  A        i    h         A  F
                 1k J  8N       N       I    IIII  I        n    f         I
                 II I  III      I                                I
     ATCCCTATTTATGGGGAAGCCAGCATCCTTTGATGCCACCATATGGGACTCCTGTCCAT       720
     ----+----+----+----+----+----+----+----+----+----+----+----+
     TAGGGATAAATACCCCTTCGGTCGTAGGAAACTACGGTGGTATACCCCTGAGGACAGGGTA
      I  P  I  Y  G  E  A  S  I  L  *  C  H  H  M  G  L  L  S  H  -
      S  L  F  M  W  G  S  Q  H  P  L  M  P  P  Y  G  T  P  V  P  Y  -
      P  Y  L  W  G  S  Q  H  P  L  M  P  P  Y  G  T  P  V  P  Y  -
661

E                                        T
                       C cBS       FM                            t  t
                      Av li        on                             h
                      uJ IJF       k1                      N  M  T
                      II III       II                      l  a  sH 1
                                                           aMPe pi 1
                                                           IslI 4n 1
                                                           IleI 5f I I
                                                           IIII II I I
     ATCCAGCTTTATATCCTCCTGGAGTATCTATGCTCATCATCCAAGCATGGCAGTGACTC        780
     ----+----+----+----+----+----+----+----+----+----+----+----+
     TAGGTCGAAATATAGGAGGACCCTCATAGATACGAGTAGTAGGTTCGTACCGTCACTGAG
      I  Q  L  Y  I  L  L  G  V  S  M  L  I  I  Q  A  W  Q  *  L  -
      S  S  F  I  S  S  W  E  Y  L  C  S  S  K  H  G  S  D  S  -
      P  A  L  Y  P  P  G  S  I  Y  A  H  H  P  S  M  A  V  T  P  -
721
``` a
b
c

Fig. 1j

```
                              B                    S
                              s       R            Ba       H
                              p       s            suPDT    i
                              G       a          B m3lpa    n f
                              I       I          c c AAenq  I
                              I       I          I I IIII   I
      CGAGTGTTGTCCAGCAAAGTACGGAGAGATTGAAGGGAAGAACTGATGAAAGGATCGAG
781   ------+---------+---------+---------+---------+---------+  840
      GCTCACACAACAGTCGTTTCATGCCTCTCTAACTTCCCTTGACTACTTCCTAGCTC
      R  V  L  S  S  K  V  R  R  L  K  G  R  E  L  M  E  R  I  E   -
      E  C  C  P  A  K  Y  G  D  *  R  E  G  N  *  W  K  G  S  R   -
      S  V  V  Q  Q  S  T  E  I  E  G  K  G  T  D  G  K  D  R  D   -

T                          B  C  C  N
                s                          s  v  v  l
      A         p                          p  i  p  a
      l         5                          M  R  H  H
      w         0                          I  I  I  V
      I         9                          I  I  I  I
      ACTCGTCCAAAAATTGAAAGGAACTTCTGCAAATGCAGGTTCCAAAGCAGGAGAGAGTG
841   ------+---------+---------+---------+---------+---------+  900
      TGAGCAGGTTTTTTAACTTTCCTTGAAGACGTTTACGTCCAAGGTTTCGTCCTCTCAC
      T  R  P  K  N  *  K  E  L  L  Q  M  Q  V  P  K  Q  E  R  V   -
      L  V  Q  K  I  E  R  N  F  C  K  C  R  F  Q  S  R  R  E  W   -
      S  S  K  K  L  K  G  T  S  A  N  A  G  S  K  A  G  E  S  G   -
``` a
b
c

Fig. 1k

```
         B              N
       C Cp             l               B                    D
       a vuD          MBs aN            s                  M r H
       c ild          wcr Is            m                  n d p
       8 JOe          ocD Ip            A                  1 I h
       I III          III II            I                  I I I
       /              /                                    /
     GAAAGGCAGGCTCAGGTTCAGGCAATGATGGCATGTCTCAAAGTGGTGAAAGTGGTTCAG
     ------+---------+---------+---------+---------+---------+    960
     CTTTCCGTCCGAGTCCAAGTCCGTTACTACCGTACAGAGTTTCACCACTTTCACCAAGTC E R Q A Q V Q A M M A C L K V V K V V Q  -
       K G R L R F R Q * W H V S K W * K W F R  -
         K A G S G G N D G M S Q S G E S G S E  -

T   BB                       H     C
              a   fs                       iT    Av
              q   am                       nf    li
              I   II                       fi    uJ
                                           II    II
              /                            /     /
     AGGGGTTCATCGAATGCTAGTGATGAGAATAATAACCAACAGGAATCAGCTACAAACAAGA
     ------+---------+---------+---------+---------+---------+    1020
     TCCCAAGTAGCTTACGATCACTACTCTTATTATTGGTTGTCCTTAGTCGATGTTTGTTCT

```
                    T                            N
                    s                            B 1
             NC     p                            a a
        B    l v    5X                           n I
        c    a i    0c                           I V
        c    i J    9m
        I    V I    I I
        T T
        t t
        h h
H i n   C S 1 1
d A v f 1 1
I l i a 1 1
I   u J N I I
I   I I I I I
    / / /
         AGGGAAGCTTTGACCTGATGCTTGTTGATGGAGCCAATGCCCAGAACAATTCTGGGGTG
1021     ----+----|----+----|----+----|----+----|----+----|----+----  1080
         TCCCTTCGAAACTGGACTACGAACAACTACCTCGGTTACGGGTCTTGTTAAGACCCCCAC
  a
  b      R  E  A  L  T  *  C  L  L  M  E  P  M  P  R  T  I  L  G  V  -
  c       G  K  L  *  P  D  A  C  *  W  S  Q  C  P  E  Q  F  W  G  C  -
           G  S  F  D  L  M  L  V  D  G  A  N  A  Q  N  N  S  G  G  A  -

E
         c B S     C                     B  C
         o s c     M v                   s  a           M
         R a r     w i                   m  c           s
         I J F     o J                   A  8           e
         I I I     I I                   I  I           I
         CCATTTCTCAATTCTTCTATGCCTGGGAAGCCTGTTGTCTCAATGCCAGCAACTAATCTTA
1081     ----+----|----+----|----+----|----+----|----+----|----+----  1140
         GGTAAAGAGTTAGAAGATACGGACCCTTCGGACAACAGAGTTACGGTCGTTGATTAGAAT
  a
  b      P  F  L  N  L  L  C  L  G  S  L  L  S  Q  C  Q  Q  L  I  L  -
  c       H  F  S  I  F  Y  A  W  E  A  C  C  L  N  A  S  N  *  S  *  -
           I  S  Q  S  S  M  P  G  K  P  V  V  S  M  P  A  T  N  L  N  -
```

Fig. 1m

```
                                                                C   B  S
                                                                v  BN  sMBf              C C B
                                           F                    i  ss  asba              AvIv s
                                           o                    R  mi  WpvN              liti m
                                           k                    I  II  IIII              uJaR A
       S                                   I                    I  II  IIII              IIII I
       s                                                           /                       //
       p      ATATTGAATGGACTTATGGAATGCATCATCCGGTGGTGGCGAAGCTGCAAAAATGAGAC
       I     ------+---------+---------+---------+---------+---------+     1200
             TATAACCTTACCTGAATACCTTACGTAGTAGGCCACCACCGCTTCGACGTTTTTACTCTG I  L  E  W  T  Y  G  M  H  H  P  V  V  A  K  L  Q  K  *  D  -
              Y  W  N  G  L  M  E  C  I  R  W  R  S  C  K  N  E  T  -
                 I  G  M  D  L  W  N  A  S  S  G  G  E  A  A  K  M  R  H  -

B
                                    s
                                   pE
                              N  B1cS                      B                       M
                              B 1  s2oc                    s5                      a
                              a a  a8Rr                    at                      e
                              n I  J6IF                    Jy                      I
       1141                   I V  IIII                    II                      I
                                     ///                    /
              ATAATCAATCTGGTGCCCCAGGAGTTGTTGCCCTTGGTGAACAATGGATACAAGATGAAC
       1201  ------+---------+---------+---------+---------+---------+     1260
              TATTAGTTAGACCACGGGGTCCTCAACAACGGGAACCACTTGTTACCTATGTTCTACTTG

```
                                                 T
                                                 t
                              M                  h              M
                              b         H        c 1            a
         C                    o         i     M AbvPl           e
         Av        E          H         n     n lfill           H
         li        a          I         f     n IIIII           I
         uJ        r                    I       //
         II        I
       / 
        GTGAGCTGAAAAGACAGAAGAGAAAACAGTCAAACAGAGAGTCAGCTAGGAGGTCAAGGT       1320
  1261  -----+---------+---------+---------+---------+---------+
        CACTCGACTTTTCTGTCTTCTCTTTTGTCAGTTTGTCTCTCAGTCGATCCTCCAGTTCCA
          V  S  *  K  D  R  R  E  R  N  S  Q  T  E  S  Q  L  G  G  Q  G
         *  A  E  K  T  E  E  K  T  V  K  Q  R  V  S  *  E  R  R  S  R  L
           E  L  K  R  Q  K  R  K  Q  S  N  R  E  S  A  R  R  V  S  R  R  L
a
b
c
                                                 T                        H
                           C                     t                        iT
                           a vD                  h 1           M B        nf
                           c id                  1 1           b s        fi
                           c 8 Je                1 1           s o        II
                           8 I                   H H   BM      I H      B r  /
                           I                          bn               s
                                                      sl               r
                                                      II               H
                                                      /
        TACGCAAGCAGGCTGAGTGCGAAGACTTACAAAGAGGGTGGAGACACTGGGAAGTGAGA        1380
  1321  -----+---------+---------+---------+---------+---------+
        ATGCGTTCGTCCGACTCACGCTTCTGAATGTTTCTCCCACCTCTGTGACCCTTCACTCT
          Y  A  S  R  L  S  A  K  T  Y  K  R  G  W  R  H  W  E  V  R
         T  Q  A  G  *  V  R  E  D  L  Q  K  R  V  E  T  L  G  S  E  N
           R  K  Q  A  E  C  E  D  L  Q  K  R  V  E  T  L  G  S  E  N
a
b
c
```

Fig. 1o

```
              E                         BC              M                           H
              c                         XAsv            b                           i
              o    DES                  mlmi            o                    B      nM    C
         T    5 7  daa                  nuAJ            I                    s      dbav
         a    I I  erp                  I I I I         I                    m      I o l i
         q    I I  I I I                                                     I      I I u J
                                                                                    I I I I
                                                                                    /
      ATCGAACACTCAGAGAAGAGCTTCAGAGAGACTTTCCGAAGAATGCGAGAAGCTTACACATCTG
1381  ------+---------+---------+---------+---------+---------+------  1440
      TAGCTTGTGAGTCTCTTCTCGAAGTCTCTCTGAAAGGCTTCTTACGCTCTTCGAATGTAGAC a    I  E  H  S  E  K  S  F  R  D  F  P  K  N  A  R  S  L  H  L   -
  b    S  N  T  Q  R  R  A  S  E  T  F  R  R  M  R  E  A  Y  T  S   *
  c    R  T  L  R  E  E  L  Q  R  L  S  E  E  C  E  K  L  T  S  E   -

T                                  S      H
            s                                  a      Ca                     B
            p    R   M                         u  ve  F                      s S
            5    l   b                         9  i I o                      at
            0    e   o                         6  J I k                      J y
            9    A   H                         I  I I I                      I I
            I    I   I                                                       /

AAAATAGTTCAATCAAGGAAGAATTGGAACGGATGTGTGGGCCAGAAGCAGTTGCTAACC
1441  ------+---------+---------+---------+---------+---------+------  1500
      TTTTATCAAGTTAGTTCCTTCTTAACCTTGCCTACACACCCGGTCTTCGTCAACGATTGG a    K  I  V  Q  S  R  K  N  W  N  G  C  V  G  Q  K  Q  L  L  T   -
  b    K  *  F  N  Q  G  R  I  G  T  D  V  W  A  R  S  C  *  P    -
  c    N  S  S  I  K  E  E  L  E  R  M  C  G  P  E  A  V  A  N  L   -
```

Fig. 1p

```
                              T
                              t
                              h
                              1           M
                              D1          n       B
                      F       d1          l       c
                      o       eI          H       c
                      k       II                  H
                      I        /
         TTGGATGACACAAAACATTTGAGTTCCTCAGTGTAGTGTTTGATGG
1501     -----+---------+---------+---------+---------+----   1546
         AACCTACTGTGTTTTGTAAACTCAAGGAGTCACATCACAAACTACC

Enzymes that do cut:

| | | | | |
|---|---|---|---|---|
| AluI | Alw21I | AlwNI | ApoI | BanI | BbvI |
| BccI | AlwI | BglII | BpmI | Bpu10I | BsaWI |
| BslI | BclI | BsmFI | Bsp1286I | BspGI | BsrI |
| BsrDI | BsmI | Cac8I | CviRI | CviJI | DdeI | DpnI | DraI |
| DrdII | BstYI | Eco57I | EcoRII | EcoRV | FokI | HaeI | HaeIII |
| HgaI | EarI | HindIII | Hinfl | HphI | ItaI | MaeII | MaeIII |
| MboII | HhaI | MnlI | MseI | Ms1I | MaeI | MwoI | NdeI |
| NlaIII | MmeI | NsiI | NspI | PflMI | PleI | PshAI | Psp1406I |
| RleAI | NlaIV | SapI | Sau3AI | ScrFI | SfaNI | SspI |
| StuI | RsaI | StyI | Tsp45I | Tsp509I | Tth111I | XcmI |
| XmnI | TaqI | TfiI |

Enzymes that do not cut:

| | | | | | | | |
|---|---|---|---|---|---|---|---|
| AatII | AccI | AflII | AflIII | AgeI | Alw44I | ApaI |
| ApaBI | AscI | AvaI | AvaII | BaeI | BamHI | BanII |
| Bce83I | BcgI | BcefI | BglI | Bpu1102I | BsaI | BsaAI |
| BsaBI | BsaHI | BscGI | BseRI | BsgI | BsiI | BsiEI | Bsp24I |
| BspEI | BspLU11I | BscRI | BsrFI | BsrGI | BssHII | Bst1107I | BstEII |
| BstXI | Bsu36I | ClaI | DraIII | DrdI | DsaI | EaeI | EagI |
| Eam1105I | EciI | Eco47III | EcoNI | EcoO109I | EcoRI | Esp3I | FauI |
| FseI | FspI | GdiII | HaeII | HgiEII | HincII | HpaI | KpnI |
| MluI | MscI | MspAlI | MunI | NarI | NciI | NcoI | NgoAIV |
| NheI | NotI | NruI | NspV | PacI | Pfl1108I | PmeI | PmlI |
| Psp5II | PstI | PvuI | PvuII | RcaI | RsrII | SacI | SacII |
| SalI | ScaI | SexAI | SfcI | SfiI | SgfI | SgrAI | SmaI |
| SnaBI | SpeI | SphI | SrfI | Sse8387I | SunI | SwaI |
| TaqII | ThaI | Tth111II | VspI | XbaI | XhoI | TaqI |

Fig. 1r

```
  1  TTGGGTCAT CTGAATAACT TGTTGGGACA TATTGTTTG  GTGCTTTTCT
 51  TTTGGTGATT GCCCTCATGG AAACAGTGAG GAAGGGAAAT CTGTTAAAAC
101  TGGAAGTCCT TCTTCACCAG CTACAACTGA ACAGACCAAT CAGACAAACC
151  AGCCTAACTT TCATGTCTAT CCTGATTGGG CTGCCATGCA GTATTATGGG
201  CCGAGAGTCA ACATTCCTCC ATACTTCAAC TCGGCTGTGG CTTCTGGTCA
251  TGCTCCACAC CCATACATGT GGGGTCCACC ACAGCCTATG ATGCCACCTT
301  ATGGCCACC  ATATGCAGCA TTTTATTCTC CTGGAGGGGT TTATACTCAC
351  CCTGCAGTTG CTATTGGGCC ACATTCACAC GGTCAAGGAG TTCCATCCCC
401  ACCTGCTGCT GGGACTCCTT CAAGTGTAGA TTCACCAACA AAATTATCTG
451  GAAATACTGA TCAAGGGTTA ATGAAAAAAT TGAAAGGGTT TGATGGGCTT
501  GCAATGTCAA TAGGCAATTG CAATGCTGAG AGTGCGGAGC TTGGAGCTGA
551  AAACAGGCTG TCGCAGAGTG TGGATACTGA GGGTTCTAGC GATGGAAGTG
601  ATGGCAACAC TGCAGGGGCT AATCAAACAA AAATGAAAAG AAGCCGAGAG
651  GAAACATCAA CCACTGATGG AGAAGGGAAA ACTGAGACAC AAGATGGGCC
701  AGTTTCCAAA GAGACTACAT CTTCGAAAAT GGTTATGTCT GCTACACCAG
```

Fig. 1s

```
751   CTAGTGTTGC AGGAAAGTTA GTTGGTCCTG TAATTTCTTC AGTTATGACC
801   ACAGCACTGG AGCTTAGGAA ACCTTTGACT GTTCATTCTA AGGAAAATCC
851   CACGAGTGCC CCACAACCTT GTGCAGCTGT GCCTCCTGAA GCTTGGTTAC
901   AGAATGAGCG TGAGCTGAAA CGGGAGAGGA GGAAACAATC TAACCGTGAA
951   TCTGCTAGAA GGTCCAGGCT GAGGAAGCAG GCCCGAGACTG AAGAATTGGC
1001  ACGAAAAGTT GAGATGTTAA CTGCTGAAAA TGTGTCACTG AAGTCAGAAA
1051  TAACTCAATT GACTGAAGGT TCTGAGCAGA TGAGGATGGA AAATTCTGCA
1101  TTTGAGGAAA AACTGAGAAA TACTCAACTG GGACAAAGGG AAGAGATAAT
1151  TTTGGACAGC ATTGACAGCA AGAGGTCTAC ACCTGTAAGT ACTGAAAATT
1201  TGCTATCAAG AGTTAATAAT TCCAGTTCTA ATGATAGAAG TGCAGAGAAT
1251  GAGAGTGATT TCTGTGAGAA CAAACCAAAT TCTGGTGCAA AGCTGCATCA
1301  ACTACTGGAT ACAAATCCTA GAGCTGATGC TGTTGCTGCT GGGTGAAACC
1351  AGTAATTGCA CTGGCTTATT ATGTAACTTT GGCATATTAC AAGTCCAAAA
1401  TTACAGCTTG GTGCTAACAG TTTTCAGAGG ATGGATCAGC TGAGTTTTAC
1451  AACCTAAATC CATCTATAGA CCAGGACTAA TTCTTTGCTT GTCAGTTTCT
```

Fig. 1t

```
1501  TAGGACATAA ACTCTGTATT TTATTAGAAT TGACAGAAAT GGATGACAAC
1551  TTTAAAGAAG TTTGTAAATG TAAGAGTATT AGGGATCTAG TTTAGATTT
1601  AAGATAGGGT TGTCAACCTC TGTATAATTG GTTGTGCATT AACTGTACTG
1651  GTGTGAA
```

Fig. 1u (Linear) MAP of: bz2a537.seq check: 360 from: 1 to: 1657 bZIP2a 5'race clone 537
top strand; combined sequences
also clone 501

With 191 enzymes: *

```
                                                    T                        B
                                                    t                        s
                                                    h                        m
                                                    1    1                   F
                                                    1    1                   I
                                                    I    I
          TTGGGTTCATCTGAATAACTTGTTGGGACATATTTGTTTTGGTGCTTTTCTTTTGGTGATT
  1       +---------+---------+---------+---------+---------+---------+    60
          AACCCAAGTAGACTTATTGAACAACCCTGTATAAACAAACCACGAAAAGAAAACCACTAA a    L  G  S  S  E  *  L  V  G  T  Y  L  F  G  A  F  L  L  V  I  -
       b      W  V  H  L  N  N  L  G  H  I  C  L  V  L  F  F  W  *  L  -
       c        G  F  I  *  I  T  C  W  D  I  F  V  W  C  F  S  F  G  D  C  -
```

```
        N         S  H               H
        Cl        a  Ca         H    i       M          C
        va        u  ve    I    n    n  P    n     C    v  C
        iI        9  iI    n    c    c  l    l     v    i  v
        t         6  JI    f    I    I  e    I     I    J  i
        I         I  II    I    I    I  I    I     I    I  I
        |         |  |     |    |    |  |    |     |    |  |
        CTGCCATGCAGTATTATGGGCCGAGAGTCAACATTCCTCCATACTTCAACTCGGCTGTGG
181     --------+---------+---------+---------+---------+---------+  240
        GACGGTACGTCATAATACCCGGCTCTCAGTTGTAAGGAGTATGAAGTTGAGCCGACACC

L  P  C  S  I  M  G  R  E  S  T  F  L  H  T  S  T  R  L  W  -
        C  H  A  V  L  W  A  E  S  Q  H  S  S  I  L  Q  L  G  C  G  -
        A  M  Q  Y  Y  G  P  R  V  N  I  P  P  Y  F  N  S  A  V  A  -

B
                                   s
                                   Ap  N         S
                  R                fL  B1   ANaT   S   C
        N         l                1U  Msa N   v1 ua  f  M    B
        l         e                Is  tIs  aa  9q  a  w  s
        a         A                I1  1XIp II6 I   N  o  l
        I         I                II  III  IVI I   I  H  I
        |         |                ||  ||| ||| ||   |  |  |
                                   //   //  // /
        CTTCTGGTCATGCTCCACACCCATACATGTGGGGTCCACCACAGCCTATGATGCCACCTT
241     --------+---------+---------+---------+---------+---------+  300
        GAAGACCAGTACGAGGTGTGGGTATGTACACCCCAGGTGTCGGATACTACGGTGGAA

```
            S   H           C               E                                                           C
            P   a   Ca      C               c   S                   H                       B S v      P
            f   u   ve      N   vI          BMo c               H   c       BMo c           p f i      s
            1   9   iI      d   it          bnR r               p   c       bnR r           m c R      t
            M   6   JI      e   Ra          vlI F               h   v       vlI F           I I I      I
            I   I   II      I   II          III I               I   I       III I           / /
        ATGGGCCACCATATGCAGCATTTTATTCTCCTGGAGGGGTTTATACTTCACCCTGCAGTTG
    301 ----+----+----+----+----+----+----+----+----+----+----+----+  360
        TACCCGGTGGTATACGTCGTAAAATAAGAGGACCTCCCCAAATATGAGTGGGACGTCAAC

M   G   H   H   M   Q   H   F   I   L   L   E   G   F   I   L   T   L   Q   L   -
         W   A   T   I   C   S   I   L   F   Y   S   P   G   G   V   Y   S   P   C   S   C   -
         G   P   P   Y   A   A   F   Y   S   P   G   G   V   Y   T   H   P   A   V   A   -

S   H                                                   B       B   H
            a   Ca          F                                       B   c   IPB s   i
            u   ve          o                                       b   c   tls p   n
            9   iI          k                                       v   c   ael M   f
            6   JI          I                                       I   I   III I
            I   II
        CTATTGGGCCACACATTCACACGTGGTCAAGGAGTTCCATCCCCACCTGCTGTGGGACTCCTT
    361 ----+----+----+----+----+----+----+----+----+----+----+----+  420
        GATAACCCGGTGTGTAAGTGTGCCAGTTCCTCAAGGTAGGGGTGGACGACCCTGAGGAA L   L   G   H   I   H   T   V   K   E   F   H   P   H   L   L   G   L   L   -
         Y   W   A   T   F   T   R   S   S   I   P   T   C   C   W   D   S   F   -
         I   G   P   H   S   H   G   Q   G   V   P   S   P   P   A   A   G   T   P   S   -
```

Fig. 1y

```
         B   H         T                       S                              T
         Hs  iT        s                       a                              s
         pm  nf        p                       BuD         M                  p
         hF  fi        5                       c3p         s                  5
         II  II        0                       1An         e                  0
                       9                       III         I                  9
                       1                                                      1
         /                                     /
    CAAGTGTAGATTCACCAACAAAATTATCTGGAAATACTGATCAAGGGTTAATGAAAAAT
421 ------+---------+---------+---------+---------+---------+ 480
    GTTCACATCTAAGTGGTTGTTTTAATAGACCTTTATGACTAGTTCCCAATTACTTTTTA

Q  V  *  I  H  Q  Q  N  Y  L  E  I  L  I  K  G  *  K  N  I  -
    K  C  R  F  T  N  K  I  I  W  K  Y  *  S  R  V  N  E  K  I  -
    S  V  D  S  P  T  K  L  S  G  N  T  D  Q  G  L  M  K  K  L  -

C  C  C           B                 C
                    v  a  v           s        p        v
                    i  c  i           r        M5       i
                    c  J  8           D        u0       R
                    II II R           H        n9       H
                       H  H                    II       I
                                               I
                                      /                 /
    TGAAAGGGTTTGATGGGCTTGCAATGTCAATAGGCAATTGCAATGCTGAGAGTGCGGAGC
481 ------+---------+---------+---------+---------+---------+ 540
    ACTTTCCCAAACTACCCGAACGTTACAGTTATCCGTTAACGTTACGACTCTCACGCCTCG

```
         C           C                    M  D                          B  B
         Av          v                    n  d                          f  c
         li          i                    l  e                          a  c
         uJ          J                    I  I                          I  I
         II          I
         TTGGAGCTGAAAAACAGGCTGTCGCAGAGTGTGGATACTGAGGGTTCTAGCGATGGAAGTG
541  ----+---------+---------+---------+---------+---------+---------+  600
         AACCTCGACTTTTGTCCGACAGCGTCTCACACCTATGACTCCCAAGATCGCTACCTTCAC

L  E  L  K  T  G  C  R  R  V  W  I  L  R  V  L  A  M  E  V  -
     W  S  *  K  Q  A  V  A  E  C  G  Y  *  G  F  *  R  W  K  *  -
     G  A  E  N  R  L  S  Q  S  V  D  T  E  G  S  S  D  G  S  D  -

T
                                            t
                                            h
                      C                     1    C
         B            S  V   P              1M   v
         c            f  i   s              1n   i
         c            c  R   t              I1   J
         H            H  I   I              II   I
         ATGGCAACACTGCAGGGGCTAATCAAACAAAAATGAAAAAGCCGAGAGAAACATCAA
601  ----+---------+---------+---------+---------+---------+------  660
         TACCGTTGTGACGTCCCCGATTAGTTTGTTTTTACTTTTCTTCGGCTCTCTTTGTAGTT

```
                    B                        S   H              B
                    s     D                  a   C a        B   s    B    M
                    m     d                  Bu  vBe        s   p    s    b
                    A     e                  c9  isI        m   2    p    o
                    I     I                  c6  JrI        A   4    A    I
         B                                   II  III        I   I    I    I
         c
         c
         I
      CCACTGATGGAGAAGGGAAAAACTGAGACACAAGATGGGCCAGTTTCCAAAGAGACTACAT
661   ---------+---------+---------+---------+---------+---------+  720
      GGTGACTACCTCTTCCCTTTTGACTCTGTGTTCTACCCGGTCAAAGGTTTCTCTGATGTA

P  L  M  E  K  G  K  L  R  H  K  M  G  Q  F  P  K  R  L  H  -
       H  *  W  R  R  E  N  *  D  T  R  W  A  S  F  Q  R  D  Y  I  -
       T  D  G  E  G  K  T  E  T  Q  D  G  P  V  S  K  E  T  T  S  -

E    S
                      C         C    C                           c    Aa   M
                M     ABv       M    v                           o    vu   b
          NT    w     lfi       w    i                           5    a9   o
          sa    o     uaJ       o    R                           7    I6   I
          pq    I     III       I    I                           I    II   I
          VI
      CTTCGAAAAATGGTTATGTCTGCTACACCAGCTAGTGTTGCAGGAAAGTTAGTTGGTCCTG
721   ---------+---------+---------+---------+---------+---------+  780
      GAAGCTTTTACCAATACAGACGATGTGGTCGATCACAACGTCCTTTCAATCAACCAGGAC L  R  K  W  L  C  L  L  H  Q  L  V  L  Q  E  S  *  L  V  L  -
       F  E  N  G  Y  V  C  Y  T  S  *  C  C  R  K  V  S  W  S  C  -
       S  K  M  V  M  S  A  T  P  A  S  V  A  G  K  L  V  G  P  V  -
``` a
b
c a
b
c

Fig. 1bb

```
          T                                           B
          s                                  B        pC         B     D
          p                                  s        BAuvD      p     d
          5                                  t        sllid      m     e
          0                                  X        ru0Je      H     H
          9                                  H        HHHHH
          H                                           //

TAATTTCTTCAGGTATGACCACCAGCACTGGAGCTTAGGAAACCTTTGACTGTTCATTCTA
781    ----+----+----+----+----+----+----+----+----+----+----+----+  840
       ATTAAAGAAGTCCATACTGGTGTCGTGACCTCGAATCCTTTGGAAACTGACAAGTAAGAT

*  F  L  Q  *  P  Q  H  W  S  L  G  N  L  *  L  F  I  L  -
          N  F  F  R  Y  D  H  S  T  G  A  *  E  T  F  D  C  S  F  *
             I  S  S  G  M  T  T  A  L  E  L  R  K  P  L  T  V  H  S  K  -

B                                 H         M
                          s                                 i         C  a
                          p                        M        n         C  ABvMe
                          1                   C    CsPR     d         I  lsinI
                          2                   v I  Avpvl    B    b    I  ugJlI
                          8                   i t  liAue    s    b    I  IIIII
                          6                   R a  uJllA    p    v    /
                          H                   II   IIIII    H    H
                                                   ////

AGGAAAATCCCACGAGTGCCCCACAACCTTGTGCAGCTGTGCCTCCTGAAGCTTGGTTAC
841    ----+----+----+----+----+----+----+----+----+----+----+----+  900
       TCCTTTTAGGGTGCTCACGGGGTGTTGGAACACGTCGACACGGAGGACTTCGAACCAATG

```
                 Bsp          MM              A                    RS          T
                 m05          nwl             cc                   sca         sp
                 09I          oII             II                   aII         pA5
                 FHI          HI              HI                   HI          oP09
                                                                               II/
                                                                               II
     AAGAGATAATTTTGGACAGCATTGACAGCAAGAGGTCTACACCTGTAAGTACTGAAAATT
1141 ----+----+----+----+----+----+----+----+----+----+----+----+ 1200
     TTCTCTATTAAAACCTGTCGTAACTGTCGTTCTCCAGATGTGGACATTCATGACTTTTAA a      K  R  *  F  W  T  A  L  T  A  R  G  L  H  L  *  V  L  K  I  -
b       R  D  N  F  G  Q  H  *  Q  Q  E  V  Y  T  C  K  Y  *  K  F  -
c        E  I  I  L  D  S  I  D  S  K  R  S  T  P  V  S  T  E  N  L  -

Tsp                                           C
                 M50                         Bsr               vi
                 se9                         09H               RH
                 HH                          IH                I

TGCTATCAAGAGTTAATAATTCCAGTTCTAATGATAGAAGTGCAGAGAATGAGAGTGATT
1201 ----+----+----+----+----+----+----+----+----+----+----+----+ 1260
     ACGATAGTTCTCAATTATTAAGGTCAAGATTACTATCTTCACGTCTCTTACTCTCACTAA a      C  Y  Q  E  L  I  I  P  V  L  M  I  E  V  Q  R  M  R  V  I  -
b       A  I  K  S  *  *  F  Q  F  *  *  K  C  R  E  *  E  S  D  F  -
c        L  S  R  V  N  N  S  S  N  D  R  S  A  E  N  E  S  D  F  -
```

Fig. 1ff

```
                              T
                              s
                    P    P    C     C  C
                    A5B  Bf   AvIv
                    p0b  sl   liti
                    o9v  1M   uJaR
                    III  II   IIII
             B  s              /  /
             s  f   C
             g  a   S
             I  N       TCTGTGAGAACAAACCAAATTCTGGTGCAAAGCTGCATCAACTACTGGATACAAATCCTA
       1261 -------+---------+---------+---------+---------+---------+ 1320
                       AGACACTCTTGTTTGTTTAAGACCACGTTTCGACGTAGTTGATGACCTATGTTTAGGAT
              S   V   R   T   N   Q   I   L   V   Q   S   C   I   N   Y   W   I   Q   I   L   –
              L   *   E   Q   T   K   F   W   C   K   A   A   S   T   T   G   Y   K   S   *   –
              C   E   N   K   P   N   S   G   A   K   L   H   Q   L   L   D   T   N   P   R   –
``` a
b
c

```
                             T                              M
                             s                              a
                   C         p     C    v           C       e
              BAv  T    a    5H    B    i           vB      H
              bli  q    MI   0p    s    9           is      I
              vuJ  H    wt   9h    r    R           Jr      I
              III  I    oa   II    I    I           II      I
              /                                             /
                          GAGCTGATGCTGTTGCTGCTGGGTGAAACCAGTAATTGCACTGGCTTATTATGTAACTTT
       1321 -------+---------+---------+---------+---------+---------+ 1380
                          CTCGACTACGACAACGACGACCCACTTTGGTCATTAACGTGACCGAATAATACATTGAAA
                E   L   M   L   L   L   L   G   E   T   S   N   C   T   G   L   L   C   N   F   –
                S   *   C   C   C   W   V   K   P   V   I   A   L   Y   Y   V   T   L   –
                A   D   A   V   A   A   G   *   N   Q   *   L   H   W   L   I   M   *   L   W   –
``` a
b
c

Fig. 1gg

```
                     T              C                       M                     S
                     s              Av                      n                     a     C
                     p              l i                     l                     Bu D  Av
                     5              u J                     I                     c3 p  l i
                     0              I I                     I                     cA n  u J
                     9              I I                     I                     I I   I I
                     I              / /                     I                     I I   I /
      GGCATATTACAAGTCCAAAATTACAGCTTGGTGCTAACAGTTTTCAGAGGATGGATCAGC
1381  ------+---------+---------+---------+---------+---------+  1440
      CCGTATAATGTTCAGGTTTTAATGTCGAACCACGATTGTCAAAAGTCTCCTACCTAGTCG

G   I   L   Q   V   Q   N   Y   S   L   V   L   T   V   F   R   G   W   I   S  -
       A   Y   Y   K   S   K   I   T   A   W   C   *   Q   F   S   E   D   G   S   A  -
       H   I   T   S   P   K   L   Q   L   G   A   N   S   F   Q   R   M   D   Q   L  -

T
                                            t   T
                 M                          h   s
                 sP                E        c   1   p
      ADFpv      B  S              c  S     o   5                              D
      ldoAu      c  f              c  o  R  r   1   0                          d
      wekll      c  c              I  I  I  I   H   9                          e
      IIIII      I  H              H  I  I  I   I   I                          I
      ///
      TGAGTTTTACAACCTAAATCCATCTATAGACCAGGACTAATTCTTTGCTTGTCAGTTTCT
1441  ------+---------+---------+---------+---------+---------+  1500
      ACTCAAAATGTTGGATTTAGGTAGATATCTGGTCCTGATTAAGAAACGAACAGTCAAAGA

```
              T                                      MDF
              s                                      sro
              p                                      eak
              5                                      III
              0                                      I
              9
              I
         TAGGACATAAACTCTGTATTTTATTAGAATTGACAGAAATGGATGACAACTTAAAGAAG
1501     ------+---------+---------+---------+---------+---------+ 1560
         ATCCTGTATTTGAGACATAAAATAATCTTAACTGTCTTTACCTACTGTTGAAATTTCTTC

*  D  I  N  S  V  F  Y  *  N  *  Q  K  W  M  T  T  L  K  K  -
          R  T  *  T  L  Y  F  I  R  I  D  R  N  G  *  Q  L  *  R  S  -
             G  H  K  L  C  I  L  E  L  T  E  M  D  D  N  F  K  E  V  -

H
                                              i
              S                               n
              Ba                              c
              suD   B     A      M            I
              t3p   f     l      s            I
              YAn   a     w      e
              III   I     I      I
              I                            /

TTTGTAAAATGTAAGAGTATTAGGGATCTAGTTTAGATTTTAAGATAGGGTTGTCAACCTC
1561     ------+---------+---------+---------+---------+---------+ 1620
         AAACATTTACATTCTCATAATCCCTAGATCAAATCTAAAATTCTATCCCAACAGTTGGAG

```
         T         C          M        R       B
         s         v          s        s       s
         p  M      i    M     e        a       r
         5  n      R    s     I        I       I
         0  l      I    e     I        I       I
         9  I      I    I     I        I       I
         H  I      I    I     I        I       I
1621  TGTATAATTGGTTGTGTGCATTAACTGTACTGGTGTGAA                1657
      -----+---------+---------+---------+---------+--
      ACATATTAACCAACACGTAATTGACATGACCACACTT
       C  I  I  G  C  A  L  T  V  L  V  *  -
       V  *  L  V  V  H  *  L  Y  W  C  E  -
         Y  N  W  L  C  I  N  C  T  G  V  -
``` a
b
c

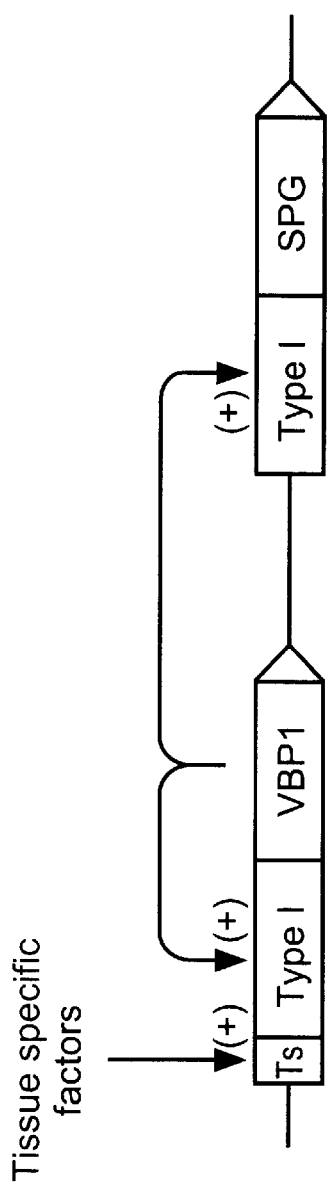
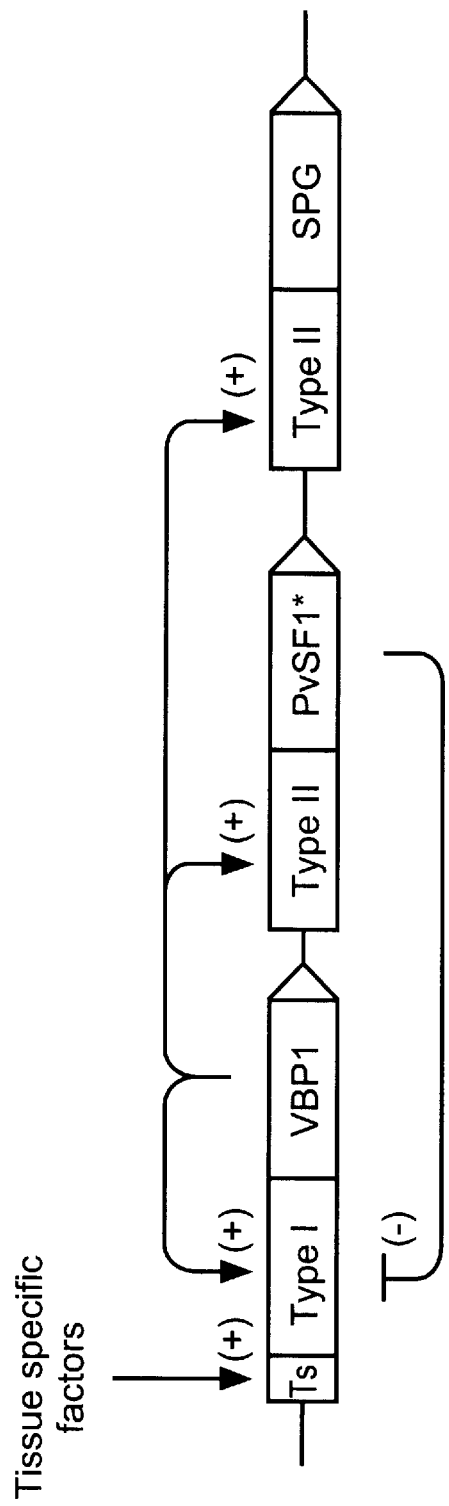
Fig. 8a
Fig. 8b

Fig. 9

The basic regions of ROM2 and ROM1.

```
                          Basic                       Leucine zipper              Target
         __αH1__ __αH2__ __αH3__|----*-------*-------*-------..  site

*   **  **                                                        1234
GCN4       DPAALKRARNTEAAARRSRARKLQRMQKL..                                       ATGAC-TCAT
         -  + +   ++ - + ++++   +   +   -  -                                     TACTG-AGTA
                                                                                     43210

*    **  **                                                   01234
ROM1    DERELKRQKRKQSNRESARRSRLRKQAECEDLQKRVETLGSENRT..                          GCCACGTCAG
        -  -+  ++ +++ + +- + ++++   +   -   -  ++ -   +                          CGGTGCAGTC
                                                                                     43210

*   **  **                                                   01234
ROM2    NERELKRQRRKQSNRESARRSRLRKQAETEELARKVEMLTAENVS..                          GCCACCTCAG
        -  -+  ++ +++ + +- + ++++   +   -   -  ++ -   -                          CGGTGGAGTC
                                                                                     43210
```

MODIFICATION OF SEED CROPS WITH TRANSCRIPTION FACTORS

This application is a continuation of application Ser. No. 08/319,544, filed Oct. 7, 1994, now abandoned.

BACKGROUND OF THE INVENTION (i) Field of the Invention

The present invention relates to regulation of genes expressed during seed maturation and, more particularly, to proteins (and corresponding DNAs) which bind with high affinity to promoter regions of genes expressed during seed maturation. The invention further relates to use of such proteins in order to enhance or reduce the expression of seed storage protein and oil-body protein genes in transgenic plants, thereby altering the protein and oil composition of the seeds.

(ii) Description of Related Art

Genes expressed specifically during seed maturation possess some of the most highly regulated promoters found in higher vascular plants. The main maturation associated products of the common bean are 7S globulin storage proteins (phaseolins) and lectins, which together represent 80% of all seed proteins.

One of the most distinctive characteristics of seed storage protein (SSP) and lectin genes and their promoters is that they are most active during seed maturation and become rapidly repressed at the time of seed abscission (Hughes & Galau, 1989; Murray & Kennard, 1984). This decreased expression of SSP and lectin genes towards the end of seed maturation distinguishes them from late embryogenesis abundant (Lea) genes which continue to be expressed throughout seed abscission (Dure. 1985). More than a decade of research into the structure and function of SSP and lectin promoters has yielded a few DNA motifs implicated in tissue-specificity and abscisic acid (ABA) inducibility (Thomas, 1993). The most abundant DNA binding activities found in developing seeds interact with AT-rich and other, apparently non-essential sequences (Jofuku et al., 1987; Bustos et al., 1991; Fujiwara & Beachy, 1994). No significant DNA binding activities have been found to interact with RY repeats of 7S and 11S SSP promoters shown to be necessary for maturation induction of those promoters in vivo (Bäumlein et al., 1992; Lelievre et al., 1992; Chamberland et al., 1992; Fujiwara & Beachy, 1994). Consequently, despite considerable efforts in that direction, cloning of maturation regulatory trans-acting factors remains an unfulfilled goal.

Except for *Brassica napus, Arabidopsis thaliana* or the legumes, the only plant species in which the molecular biology of seed maturation has been investigated in detail are the cereals, mainly wheat, rice and maize. Loss-of-function mutations at the maize Opaque2 locus are associated with an 80% reduction in the synthesis of 22 kDa zeins in the endosperm of corn kernels (Motto et al., 1988). The Opaque2 gene (Schmidt et al., 1990) encodes a transcription factor that binds to and activates the promoters of 22 kDa zein (Schmidt et al., 1992; Yunes et al 1994) and 32b (Lohmer et al., 1991 ) genes, but has little effect on the expression of 19 kDa zein genes. Recombinant Opaque2 protein expressed as a fusion with *E. coli* galactosidase binds to the sequence [SEQ ID NO.:1] $5'$CAC<u>ACGT</u>CAA$^{3'}$ of the δ-phaseolin promoter; more importantly, nuclear factors present in immature bean cotyledons also bind to this motif, and display the same apparent sequence specificity as Opaque2 (Bustos et al., submitted), suggesting that Opaque2-like proteins may be involved in phaseolin regulation. Opaque2 belongs to the family of basic-leucine zipper (bZIP) transcription factors. Plant bZIP factors form a heterogeneous family of proteins that commonly bind to DNA sequences containing a $5'$ACGT$^{3'}$ core (Weisshaar et al., 1991; Foster et al., 1994). The bZIP domain consists of a basic region and an amphipathic α-helical segment containing three or more heptad repeats of leucine residues (leucine zipper). The basic region contacts the DNA double-helix, and the leucine zipper functions as a dimerization domain.

From the above discussion, it should be apparent that regulation of genes expressed during seed maturation has yet to be achieved given the failure of the art to identify and characterize those proteins serving such a regulatory function. Indeed, it has been found that in most agronomically important plants, seed storage proteins and oil-body proteins are encoded by "gene families," i.e., sets of a few to hundreds of genes. In order to effect significant changes in seed protein or oil compositions, therefore, it is necessary to simultaneously alter the activity of potentially large numbers of genes at once. This to date has presented an obstacle to genetic engineering of seed crops. For this reason, the numerous important commercial implications stemming from control of this regulatory function, such as control of the oil and protein content of a seed, have not been realized.

SUMMARY AND OBJECTS OF THE INVENTION

In view of numerous obstacles encountered to date in the regulation of genes expressed during seed maturation, as well as other disadvantages not specifically mentioned above, it should be apparent that there still exists a need in the art for regulation of seed maturation genes which does not require control of the potentially hundreds of genes, i.e., the "gene families," often involved in such maturation processes in a seed. It is, therefore, a primary object of the present invention to fulfill that need by providing suitable trans-acting factors which have the ability to coordinately regulate entire sets of genes.

More particularly, it is an object of the present invention to provide transcription factors cloned from a seed crop that are expressed in developing seeds and whose target genes are seed storage proteins, lectins and oil-body proteins.

A further object of the present invention is to provide transcription factors which interact with the promoters of seed storage protein and lectin genes and which recognize identical or similar sequences of nucleotide base pairs in the promoters of other known genes from soybean, bean, broad bean, and pea.

Yet another object of the present invention is to provide a transcription factor which can be used to transform a host plant, such as soybean or bean plants.

Another object of the present invention is to provide high level expression cassettes for production of natural products.

In a first aspect, the present invention relates to an isolated transcription factor gene which is expressed in a maturing dicot seed and which encodes a transcription factor protein which targets a promoter of a gene encoding seed storage proteins, lectins or oil-body proteins. The transcription factor can be one which binds to 7S globulin (b-phaseolin) or lectin (PHA-L) promoters. Preferred genes include Pv Seed Factor-1 (ROM1) and Vicilin-box Binding Protein-1 (ROM2). The seeds are preferably legumes and especially, soybean, (*Glycine max*), beans (*Phaseolus vulgaris*), broad beans (*Vicia faba*) or peas (*Pisum sativum*).

In a second aspect, the present invention relates to a recombinant vector including the transcription factor gene described above. The vector is suitable for transforming a dicot seed crop.

In a third aspect, the present invention relates to an isolated or recombinantly expressed transcription factor protein encoded by the transcription factor gene described above.

In a fourth aspect, the present invention relates to a method for enhancing or reducing expression of seed storage protein, lectin or oil-protein genes in dicot seed crops comprising transforming a seed crop plant with the transcription factor gene described above such that the plant expresses the transcription factor protein encoded by the transcription factor gene.

In another aspect, the present invention relates to a recombinant dicot seed crop plant transformed with the transcription factor described above.

In a final aspect, the present invention relates to an expression cassette including the gene described above.

BRIEF DESCRIPTION OF THE DRAWINGS

FIG. 8 depicts expression cassettes including both ROM1 and ROM2.

FIG. 9 [SEQ ID NOS.: 30–32] depicts the basic regions of ROM2 and ROM1.

DETAILED DESCRIPTION OF PREFERRED EMBODIMENTS

Figure 1C:
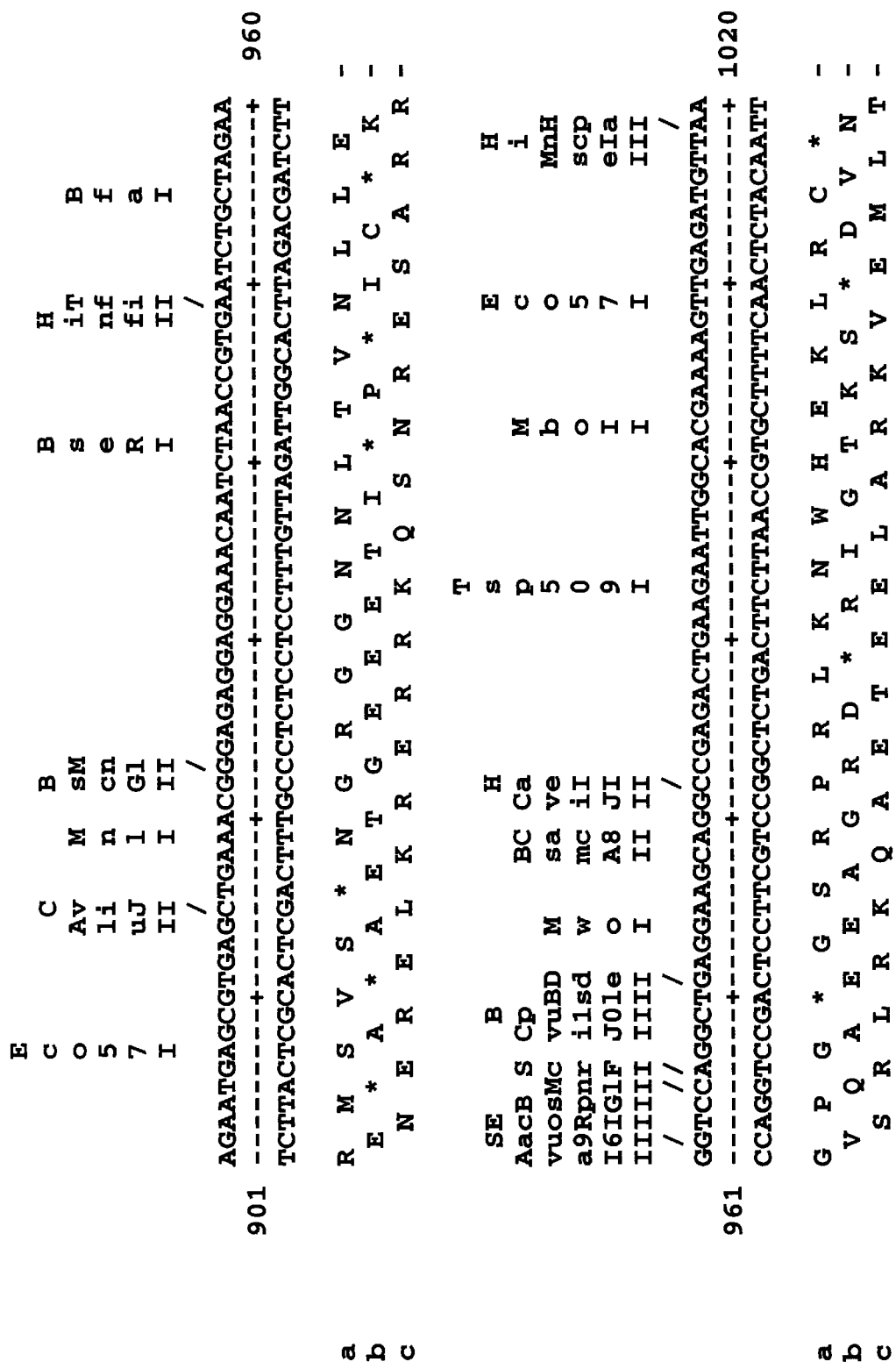
FIG. 1(a)–(ii) shows the amino acid sequences [SEQ ID NOS.: 22–29] for bZIP1 and bZIP2 deduced from the nucleotide sequences of cDNAs 1.

Initially, there will be described the cloning of a transcription factor from a seed crop, the transcription factor being one which is expressed in a maturing seed and which encodes proteins whose target genes are seed storage proteins, lectins or oil-body proteins. Although described with respect to beans, it will be appreciated that the techniques employed herein are applicable to other seed crops. Indeed, as described later, the transcription factors of the invention can be used as molecular probes to isolate equivalent genes from other seed crops.

Throughout the present application, there is employed the term bZIP which refers to a basic leucine-zipper. As described above, plant bZIP factors form a heterogeneous family of proteins that commonly bind to DNA sequences containing a $^{5'}$ACGT$^{3'}$ core. Sequence comparisons of cloned plant bZIP proteins have revealed a highly conserved segment of 15 amino acids within the basic domain (See FIG. 9). We took advantage of this conservation to clone bZIP-related cDNAs from bean embryos.

Two different bZIP genes have been isolated whose protein products bind specifically to 7S globulin (δ-phaseolin) and lectin (PHA-L) promoters. One of these genes, VBP1, recognizes a broad range of conserved sequences, collectively known as vicilin-boxes, located within the proximal 300 bp of bean seed storage protein (SSP) and lectin promoters. Many other maturation-specific promoters contain similar or identical VBP1 sites which often appear next to conserved RY repeats suggesting an interaction between VBP1-like proteins and putative RY-specific factors.

METHODS

Plant materials

*Phaseolus vulgaris* cv. Tendergreen plants were grown under standard greenhouse conditions. Dissected embryos, leaves and roots were harvested, immediately frozen in liquid $N_2$ and stored at 70° C. until used.

Primers

Primer sequences [SEQ ID NOS.: 2–3] used in the experiments are listed as follows. (dT) 17-adaptor primer for cDNA synthesis: 5'-GAC TCG AGT CGA CAT CGA TTT TTT TTT TTT TTT TT-3'; adaptor primer: 5'GAC TCG AGT CGA CAT CGA-3'. Degenerate bZIP gene-specific primers, deduced from the consensus amino acid sequences [SEQ ID NO. 4] (RK[Q/E/L]SNRESARR) of the basic domain of plant bZIP genes were synthesized as two nested sets of oligonucleotides. In order to lower the degeneracy of the primers, only the most frequently used codons were included. To further reduce the number of possible permutations each primer was synthesized as two subsets with the sequences [SEQ ID NOS.: 5≧8] 5'-AGR AAR SWD TCH AAY AG-3' (olbZlPd6), 5'-AGR AAR SWD TCH AAY CG-3' (olbZlPd7) and 5'-MGD GAR TCH GCH AGR AG-3' (olbZIPd3), 5'-MGD GAR TCH GCH AGR CG-3' (olbZIPd4). Primers olbZIPd6 and olbZIPd7 correspond to the amino acid sequence RKQ/E/LSNR, and olbZIPd3 and olbZIPd4 to RESARR.

The 5'RACE reaction for each PvbZIP clone employed two gene-specific primers [SEQ ID NOS.: 9–13]: 5'-ATT ACA ATT GAG GGT TA-3' (PvbZIP1 downstream primer), 5'-CCA TCA AAC ACT ACA CTG AG-3' (PvbZIP1 upstream primer); 5'-ACT CAG ATA CCA TTA GA-3' (PvbZIP2 downstream primer), 5'-TTC ACA CCA GTA CAG TTA AT-3' (PvbZIP2 upstream primer A), 5'-CCC AGT TGA GTA TTT CTC AG-3' (PvbZIP2 upstream primer B). PvbZIP2 primer A anneals to the 3'-untranslated region while primer B anneals to a coding region located right after the bZIP domain.

Primers for amplification of the proximal promoter (-256 to -5) of the PHA-L gene from Tendergreen genomic DNA have the sequences [SEQ ID NOS.: 14–15] 5'-GGA AGC TTA GTA ACA TCT GCA CTG TGG-3' (upstream primer) and 5'-GGT CTA GAC CAT CAT TCT CTT CTC TCT A-3' (downstream primer).

3' RACE

Total RNA was isolated from bean embryos (15 mm in length) using the guanidinium thiocyanate/cesium chloride method (Sambrook et al. 1989) and poly(A)+ RNA was selected using the PolyATract mRNA isolation system (Promega). First strand cDNA was synthesized according to the SUPERSCRIPT Preamplification System (BRL) with the following modifications: 500 ng of poly(A)+ RNA were used in each reaction, the $(dT)_{17}$-adaptor (1 µg/µl) was substituted for the oligo(dT)$_{12-18}$ primer, and the reaction was incubated at 42° C. for 2 hr. The 3' RACE protocol was as described by Frohman et al. (1988) with the following modifications: after synthesis of the cDNA first strand, the reaction mixture was diluted to 2 ml with TE (IOmM Tris-HCl, pH 8.0; 1 mM EDTA) and concentrated with Centricon-30 (Amicon) to purify the cDNA; this step was repeated two more times. The final cDNA pool had a volume of approximately 50 µl and was stored at -20° C.

Amplification was carried out by running two nested 3' anchored PCR reactions using the adaptor primer and two bZIP-specific primers deduced from the basic region. The primary 3' RACE reaction was done using 3 to 5 µl of the first strand cDNA pool, 2 pmol of adaptor primer, and 50 pmol of degenerate gene-specific primer in a 50 µl reaction mixture, containing 2.5% formamide, 200 nM dNTPs, 1.5 mM $MgCl_2$, and 2.5 units of the Taq DNA polymerase (Promega) and its buffer. The reaction was set up first without the adaptor primer and run at 94° C. for 4 min, 52° C. for 5 min, and 72° C. for 20 min to extend the second cDNA strand using the degenerate bZIP-specific primer. The adaptor primer was then added and the reaction was completed by running 35 cycles (94° C., 2 min ; 52° C., 2 min; 72° C., 2 min) of amplification followed by 10 min of extention at 72° C. The PCR product was purified with Centricon-30 and 1 µl was used for the second, nested PCR reaction, which was carried out for 30 cycles under the same amplification conditions. The final PCR products were cloned into the PCRII vector (TA cloning kit; Invitrogen) and those larger than 400 bp were partially sequenced. Peptide sequences derived from these clones were compared to known plant bZIP proteins to select the ones that contained a putative bZIP domain.

5' RACE

5' RACE reactions were carried out using the 5' RACE system from BRL. Due to the difficulty of obtaining products longer than 1.6 kb in 5' RACE, two PCR reactions were performed separately for PvbZIP2 using cDNA, which was synthesized with the downstream gene-specific primer, and PvbZIP2 upstream primer A and primer B, respectively.

DNA sequencing

Sequencing was done in plasmids using the dideoxy-sequenase method (USB). Both strands of the PvbZIP clones were sequenced with synthetic oligonucleotides as primers.

RNA blot

Total RNA samples were isolated from leaves, roots of young mature plants, and embryos of different developmental stages using a hot phenol/SDS method as described in Meier et al. (1993). RNA samples were run on a 1.0% formaldehyde denaturing agarose gel (Sambrook et al. 1989), visualized by staining with acridine orange to confirm equal loadings, transferred to a nylon filter (Nytran; S&S), and hybridized by incubating at 43° C. for 24 hr to random-primed (USB), $^{32}$P-labeled probes. The hybridization solution contained 50% formamide, 3% SDS, 6X SSPE, 5X Denhardt's solution, and 10% dextran sulfate. The filter was washed at 40° C. twice with 2X SSPE/0.1% SDS, once with 1X SSPE/0.1% SDS, and once with 0.2X SSPE/0.2 % SDS for 10 min each.

Expression of recombinant protein in E. coli

The bZIP domain-containing C-terminal portion of PvbZIP1 (aa 247 to 339) and that of PvbZIP2 (aa 268 to 424) were PCR amplified and cloned into the NdeI and BamHI sites in the pET15b vector (Novagen). The junction as well as the bZIP domain regions of each construct were sequenced to verify the correct open reading frames. The constructs were used to transform the expression host BL21 (DE3)/pLysS and transformants were verified by PCR. Culturing for induction of expression from transformed BL21 (DE3)/pLysS cells employed 100 ml of TB medium (Sambrook et al. 1989). When $OD_{600}$ of the culture reached 0.6, expression was triggered by adding I mM of IPTG to the culture medium. The incubation was continued for an additional 2 hr at 37° C. Induced bacterial cells were harvested, freeze-thawed three times, and sonicated in sonication buffer (50 mM sodium phosphate, pH 8.0; 300 mM NaCl; 0.1 % Triton X-100; 0.5 mM PMSF). The mixture was centrifuged and fusion proteins were purified on a $Ni^{2+}$-NTA-agarose affinity column according to the manufacturer (Qiagen). Isolated proteins were dialyzed into protein buffer (20 mM HEPES, pH 7.9; 50 mM KCl; 10% glycerol; 0.1 mM $Na_2EDTA$; 0.5 mM DTT; 0.5 mM PMSF) and stored at -70° C.

Electrophoresis mobility shift assay

The PHA-L promoter fragment was amplified from Tendergreen genomic DNA with primers described above, purified from a polyacrylamide gel, and cloned into the pT7Blue vector (Novagen). For making a PHA-L probe, the plasmid was digested by SpeI, labeled by filling in with ($\alpha$-$^{32}$P) dCTP with the Klenow enzyme (USB), and cut by EcoRI to release the probe. The probe was subsequently purified on a 5% polyacrylamide gel and resuspended in STE (10 mM Tris-HCl$_1$, pH 8.0; 1 mM EDTA; 50 mM NACl) buffer to a concentration of approximately 15,000 cpm/µl. UAS1 (-302 to -64), Vbl (135 to -64), and Vb3 (-302 to -198) probes were prepared by linearizing the plasmids, labeling at 3' ends, releasing the inserts with another enzyme, and isolating the probes from a gel as described. The Vbl-46 oligonucleotide probe (-143 to -100) was prepared by annealing of two overlapping single stranded oligonucleotides together, filling in with the Klenow enzyme, and isolation of the probe from a polyacrylamide gel.

Protein-DNA binding reactions were done by incubating for 20 min at room temperature except for the Vbl-46 oligo probe, which was incubated on ice with protein. The reaction mixture was set up by adding 1.5 µl of 0.5 M NaCl, 1.0 µl of 1 µg/µl poly(dIdC), 1.0 µl (15,000 cpm) of probe DNA, 1.5 µl of 1OX binding buffer (100 mM Tris-HCl, pH 7.5; 500 mM NaCl; 25 mM $MgCl_2$; 5 mM DTT), 5 µl of protein in protein buffer (as described above), and $H_2O$ to make up to 15 ml. In the case of competition experiments, cold competitors were mixed with the probe before adding protein. The protein-DNA mixture was run on a 4 to 5% nondenaturing polyacrylamide gel in 0.5X TBE buffer. The gel was dried on a 3 mm filter paper and autoradiographed.

DNAse I footprinting assay

Probes were end-labeled as described above. For DNAse I footprinting experiments, the protein-DNA binding reaction was scaled up to 20 μl. The protein-DNA mixture was incubated on ice for 20 min and at room temperature for another 10 min before treatment with DNAse I. DNAse I digestion was done as recommended by the supplier (Pharmacia). Briefly, to each tube of the protein-DNA mixture DNAse I was added in a 30 μl volume (containing 0.6 U of DNAse I, 1.67 mM $MgCl_2$, 0.83 mM $CaCl_2$; pre-warmed to room temperature) and mixed by pipeting up-and-down three times. After a 60 sec digestion the reactions were stopped with 130 μl of DNAse I stop solution (384 mM sodium acetate, 64 mM EDTA, 0.28% SDS, 128 μg/ml yeast RNA) containing 100 μg/ml proteinase K. The mixture was then incubated at 37° C. for 10 min and extracted once with 180 μl of phenol/chloroform (50:50). The DNA was recovered from the aqueous phase by adding 360 μl of ethanol, mixing, incubating for 30 min at room temperature, and spinning (12,000 rpm) for 5 min at room temperature. The DNA was rinsed with 70% ethanol, air dried, and resuspended in 3 μl of loading dye (95% formamide, 20 mM EDTA, 0.05% bromophenol blue, and 0.05% xylene cyanol FF). The resuspended DNA was heated for 2 to 3 min at 80° C., cooled immediately on ice, and run on a 6% sequencing gel along with DNA markers from the Maxam and Gilbert sequencing reactions. The gel was dried and autoradiographed. Alternatively, the radioactive bands were scanned and quantitated with a phosphorimager (Molecular Dynamics).

EXAMPLE 1

Cloning of embryo-expressed bZIP factors from the common bean (*P. vulgaris*)

Bean nuclear proteins bind to the motif 5'CAC ACGTCAA3' in UAS1 (Bustos et al., 1991) and the same site is recognized by a recombinant Opaque2 protein (Bustos et al., submitted). This observation suggested that bZIP protein(s) might be involved in regulating phaseolin expression. To clone bean bZIP proteins expressed in developing cotyledons at the time of seed maturation, we employed a strategy based on the Rapid Amplification of cDNA Ends (3'-RACE) technique as described above. Degenerate oligonucleotide primers were synthesized corresponding to the sequence RK[Q/E/L]SNRESARR found in the basic domain of plant bZIP genes whose target sites resemble G- or C-boxes (Methods). These primers were used to amplify a set of 3'-clones containing open reading frames (ORFs) for bZIP domains. Direct sequencing of individual clones revealed that they corresponded to two different genes (or gene families), designated as bZIP1 and bZIP2.

From the nucleotide sequences of 3' clones, gene-specific primers were designed to amplify corresponding 5' segments. After identifying clones that appeared to contain full ORFs, new 5' gene specific primers were synthesized and used to re-isolate the complete ORFs starting from fresh polyA+RNA. To guard against the possibility of PCR-induced mutations, the last step was repeated with two different thermo-stable DNA polymerases (Taq and Pfu) and several clones from each were fully sequenced. All PCR clones contained single ORFs. A few silent, single base substitutions were found, one of the bZIP2 clones had a substitution of $Asn_{174}$ to $Ser_{174}$ and a 6 bp insertion between codons 21 and 22. Amino acid sequences for bZIP1 and bZIP2 deduced from the nucleotide sequences of cDNAs are shown in FIG. 1. These sequences were compared to those of other known plant bZIP proteins using PILEUP (University of Wisconsin Genetics Computer Group). bZIP2 is most closely related (87.5% identity) to GmGBFb, a protein that recognizes G-box-like elements on the promoter of an auxin-induced gene from soybean (GenEMBL accession number LO 1448).

EXAMPLE 2 bZIP1 and bZIP2 mRNAs are differentially regulated during bean seed maturation

Figure 2:
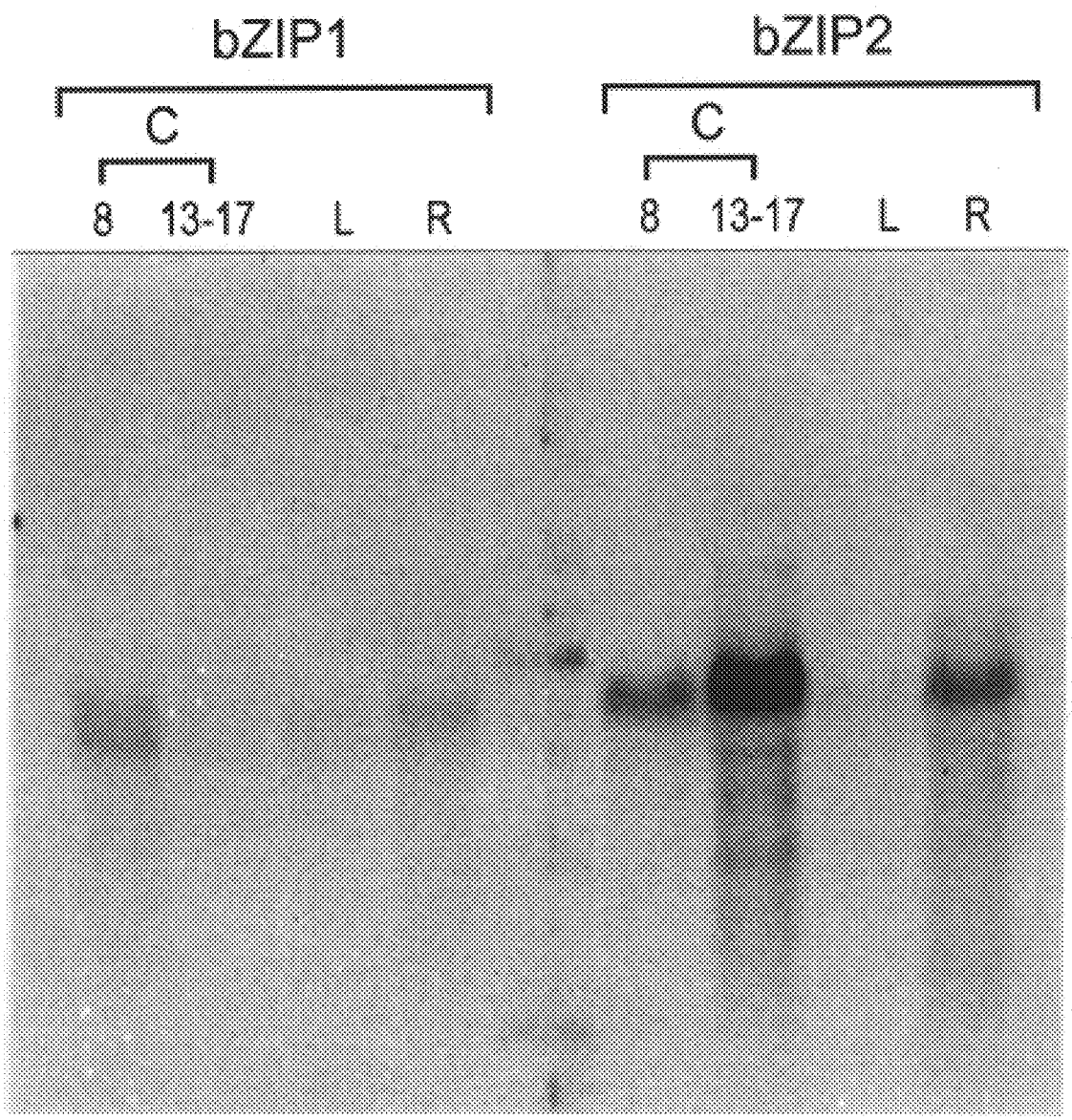
FIG. 2. Northern blot analysis of PvbZIP1 and PvbZIP2 mRNA. All RNA samples were run on the same gel and blotted to a filter. The filter was cut into two halves, one hybridized to PvbZIP1 (A) and the other to PvbZIP2 probe (B). Equal amount (6 μg) of total RNA was loaded on each lane. Lanes $E_8$ and $E_{15}$ are RNA samples from embryos with average cotyledon lengths of 8 and 15 mm, respectively. L: leaf, R: root.

The expression of bZIP1 and bZIP2 genes was studied at the mRNA level in developing embryos, leaves and roots. Total cellular RNAs were extracted, separated by agarose gel electrophoresis, blotted onto nylon membranes and separately hybridized to bZIP1 and bZIP2 probes under high stringency conditions. Autoradiographs are shown on FIG. 2. The cotyledons contain major transcripts of 1.9 and 2.1 kb which are in agreement with the lengths of bZIP1 and bZIP2 cDNAs, respectively. The steady state level of bZIP1 mRNA peaks early, in 8–11 mm cotyledons, and decreases during the course of seed maturation. In contrast, the steady-state level of bZIP2 mRNA increases after the onset of seed storage protein synthesis and peaks during the 13–17 mm stage, coinciding with the period of maximal accumulation of phaseolin and PHA mRNAs. This analysis demonstrated that bZIP2 expression is more closely correlated with the activation of phaseolin and lectin genes.

Exceedingly low levels of both mRNAs were barely detectable in leaves. However, moderate amounts of bZIP1 and bZIP2 cross-hybridizing RNAs were found in roots. Screening of a Phaseolus genomic library has yielded three different bZIP2 clones. At present, we ignore whether cotyledon and root bZIP2 transcripts are derived from the s ame or different genes.

EXAMPLE 3

Recombinant bZIP2 protein expressed in *E. coli* binds to the vicilin-box

Figure 3A:
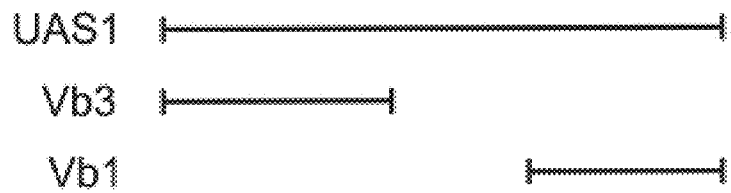
FIGS. 3A–3B. Electrophoresis mobility shifts of UAS1, Vb1 and Vb3 on binding to PbZIP1 and PvbZIP2. Probes containing UAS 1 (−302 to −64), Vb 1 (−135 to −64), and Vb3 (−302 to −198) fragments, respectively, were incubated with different E coli. expressed recombinant proteins and run on a polyacrylamide gel in 0.8X TBE buffer. Approximately 35 ng of isolated protein was used in each lane. δ-gal, protein isolated from the same expression host strain (methods) expressing recombinant δ-galactosidase from the pET15b vector and used here as a negative control.
Figure 3B:
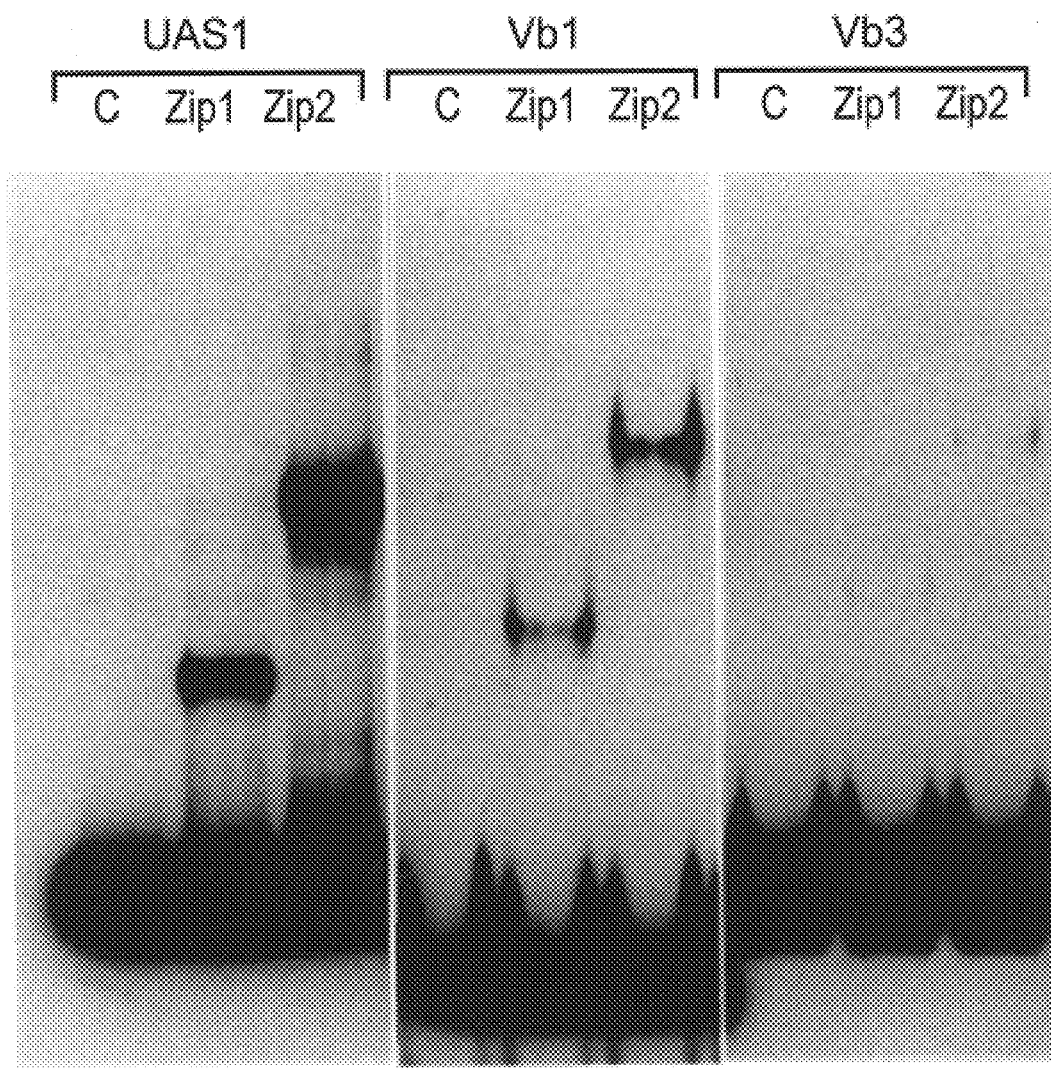

To study the binding of cloned bZIP factors to maturation-regulated genes, $His_6$-tagged polypeptides comprising putative bZIP domains plus a C-terminal tail were expressed in *E. coli*. Native proteins were recovered from *E. coli* cells and purified on a Ni+-agarose affinity column (Qiagen). Three different phaseolin promoter fragments UAS1, Vb3 and Vb1, shown on FIG. 3A, were used as probes in electrophoretic mobility shift assays. An example of such an experiment is illustrated in FIG. 3B. Both proteins formed stable complexes with all three probes albeit with different efficiencies. Under the conditions used in these experiments (probe specific activities differed by a factor of 2 at most) both proteins bound to probe Vb3 more weakly than to the other two probes.

Figure 4:
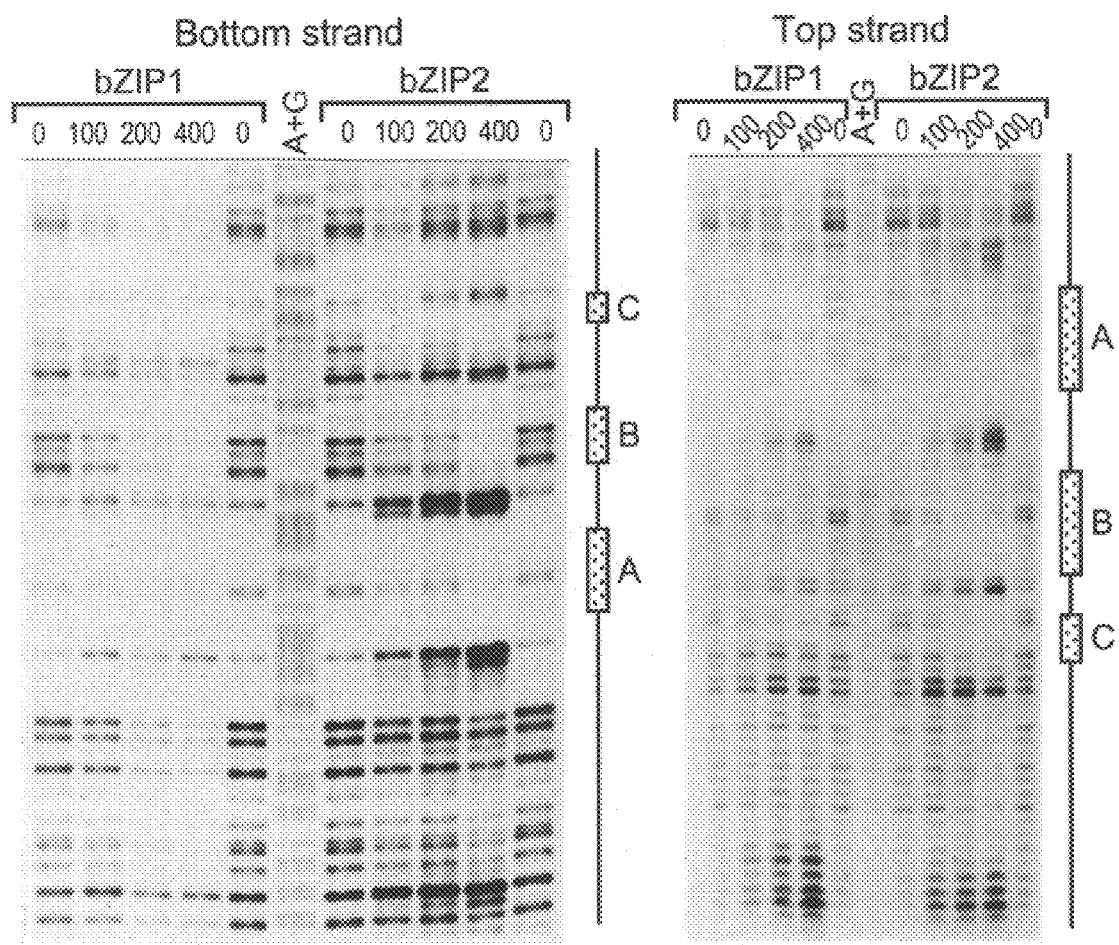
FIG. 4. DNAse I footprints of bZIP1 and bZIP2 on the UAS1 region. A 320 bp Cla I/Sac I fragment containing the UAS I (−302 to −64) fragment, released from Bluescript II SK- and labeled at the bottom strand, was used in panel A; another 311 bp Xba I/Xho I fragment containing the same UAS1 fragment labeled at the top strand was used in panel B. The number on top of each lane represents the amount of bZIP protein in nanogram used in binding reaction; lanes A+G are the Maxam and Gilbert sequencing ladders. The boxes beside each panel indicate regions protected from DNAse I digestion; induced hypersensitive sites were denoted by asterisks.
Figure 4:
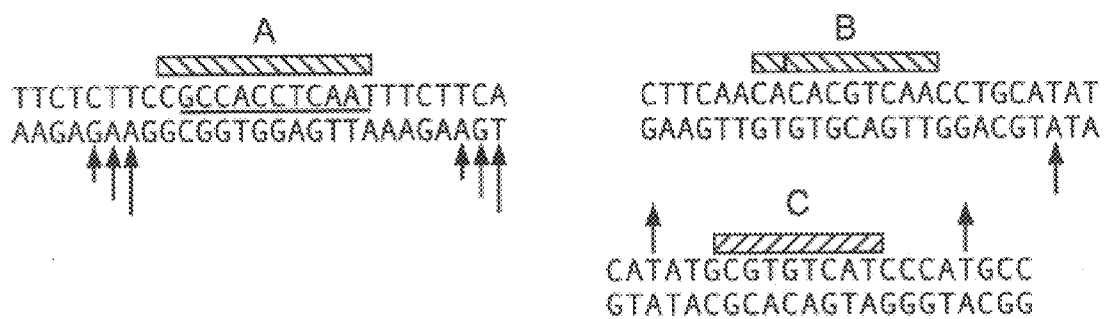
Figure 5:
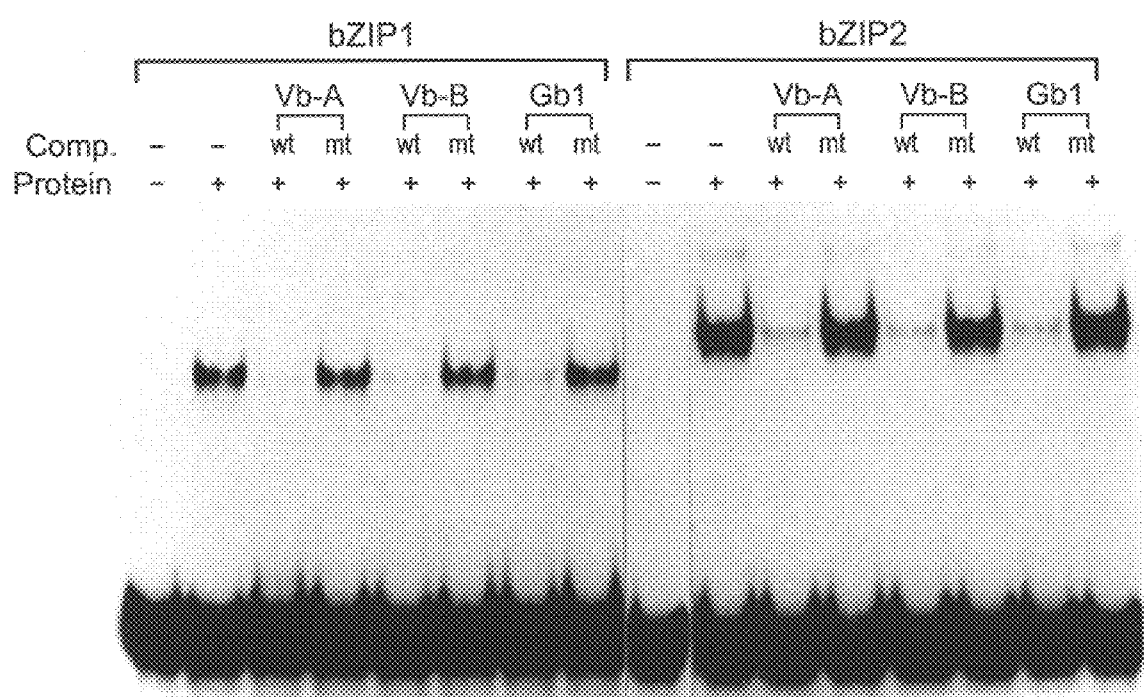
FIG. 5 depicts gels for bZIP1 and bZIP2 proteins.

The interaction of recombinant bZIP polypeptides with UAS1 was analyzed in closer detail by means of DNAseI footprinting. As shown on FIG. 4, bZIP2 yielded a strong pattern of DNAseI protection (stippled boxes) and induced hypersensitivity. The bZIP1 polypeptide produced only weak footprints. The interaction extends over the region between nucleotides −137 and −104, encompassing three full helical turns. Protected areas are centered over the vicilin-box [SEQ ID NO.: 16] 5'GCCACCTCAA3' (site A) and related motifs [SEQ IS NO.: 1] 5'CAC<u>ACGT</u>CAA3' (site B) and [SEQ ID NO.: 17] 5'GCGTGTCAT3' (site C). Site B is also recognized by the maize Opaque2 protein. These areas of protection are flanked by sites of induced hypersensitivity to DNAseI (arrows). Consistent with the binding of bZIP2 to probe Vb3 (FIG. 3B) seen by the EMSA technique, a weaker footprint was observed next to the sequence [SEQ ID NO.: 18] 5'AACACGTGCT3' (Gb 1), at position −249.

Figure 6:
FIGS. 6A–6B depicts results of testing the DNA binding specificity of each bZIP recombinant protein. The proteins were incubated with a [$^{32}$P]-labeled probe in the presence of a molar excess of either wild-type or mutant competitor DNAs. In the mutant competitors Am, Bm and Dm, the central six base pairs of each site were changed to the sequence $^{5'}$ACTAGT$^{3'}$ (FIG. 6A). The result of binding competition is shown on FIG. 6B.

EXAMPLE 4 bZIP proteins, interact with the phaseolin promoter in a sequence specific manner To test the DNA binding specificity of each bZIP recombinant protein, they were incubated with a [$^{32}$P]-labeled probe in the presence of a molar excess of either wild-type or mutant competitor DNAs. The probe used in these experiments was a synthetic, 46 bp oligonucleotide encompassing phaseolin sites A (vicilin-box) and B. Each wild-type competitor DNA contained only a single site (A, B or D). In the mutant competitors Am, Bm and Dm, the central six base pairs of each site were changed to the sequence 5'ACTAGT3' (FIG. 6A). The result of binding competition is shown on FIG. 6B. The three wild-type oligonucleotides prevented binding by either protein to the probe, while neither of the three mutants competed effectively. Identical results were obtained with both proteins at all three sites. When compared to the more sensitive DNAseI footprinting assays, competition experiments failed to detect differences in the apparent affinity of each protein for either site; this can be attributed to the molar excess (~300 fold) of competitor DNA that is required to deplete active proteins from each reaction. Nevertheless, these experiments demonstrated that bZIP1 and bZIP2 bind specifically to sites A, B and Gbl of the phaseolin promoter.

Based on their distinct expression profiles and DNA binding characteristics we propose using the names Vicilin-box Binding Protein-I ROM2 to designate factor bZIP2, and *P. vulgaris* Seed Factor-I ROM1 for factor bZIP1.

EXAMPLE 5

ROM2 and ROM1 proteins also bind to the promoter of a bean lectin promoter, PHA-L Seed lectins are well known carbohydrate binding proteins found in many plants. Because of their ability to cause aggregation of red and white blood cells, bean lectins have been termed phytohemagglutinins (PHA). PHA isoforms L and E are the second most abundant proteins in mature bean seeds (Sun et al., 1978). Together with phaseolins they account for up to 70–80% of the total protein of a mature seed. Naturally, these two gene families are also responsible for most of the transcriptional activity of mid-maturation stage embryos.

The promoter for PHA-L (Hoffman and Donaldson, 1985) contains three potential VBPl binding sites whose sequences are very similar to the phaseolin vicilin-box. To investigate whether these sites are also targets for ROM2 and ROM1, a PHA-L promoter fragment was isolated from cultivar Tendergreen by PCR amplification of genomic DNA. Binding of bacterially expressed ROM2 and ROM1 to the PHA-L probe was tested first using the EMSA technique, shown on FIG. 6. The appearance of multiple retarded bands is consistent with protein binding at more than one site.

Figure 7A:
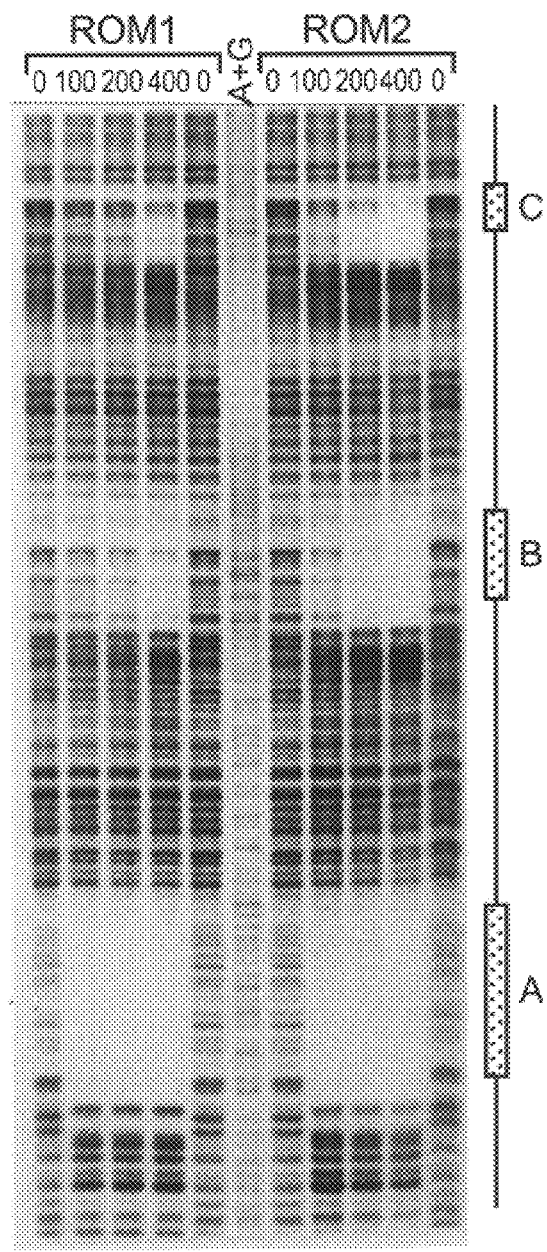
FIG. 7 shows that ROM2 and ROM1 recognize sites A, B and C corresponding to the three putative PHA-L vicilin-box sites
Figure 7B:
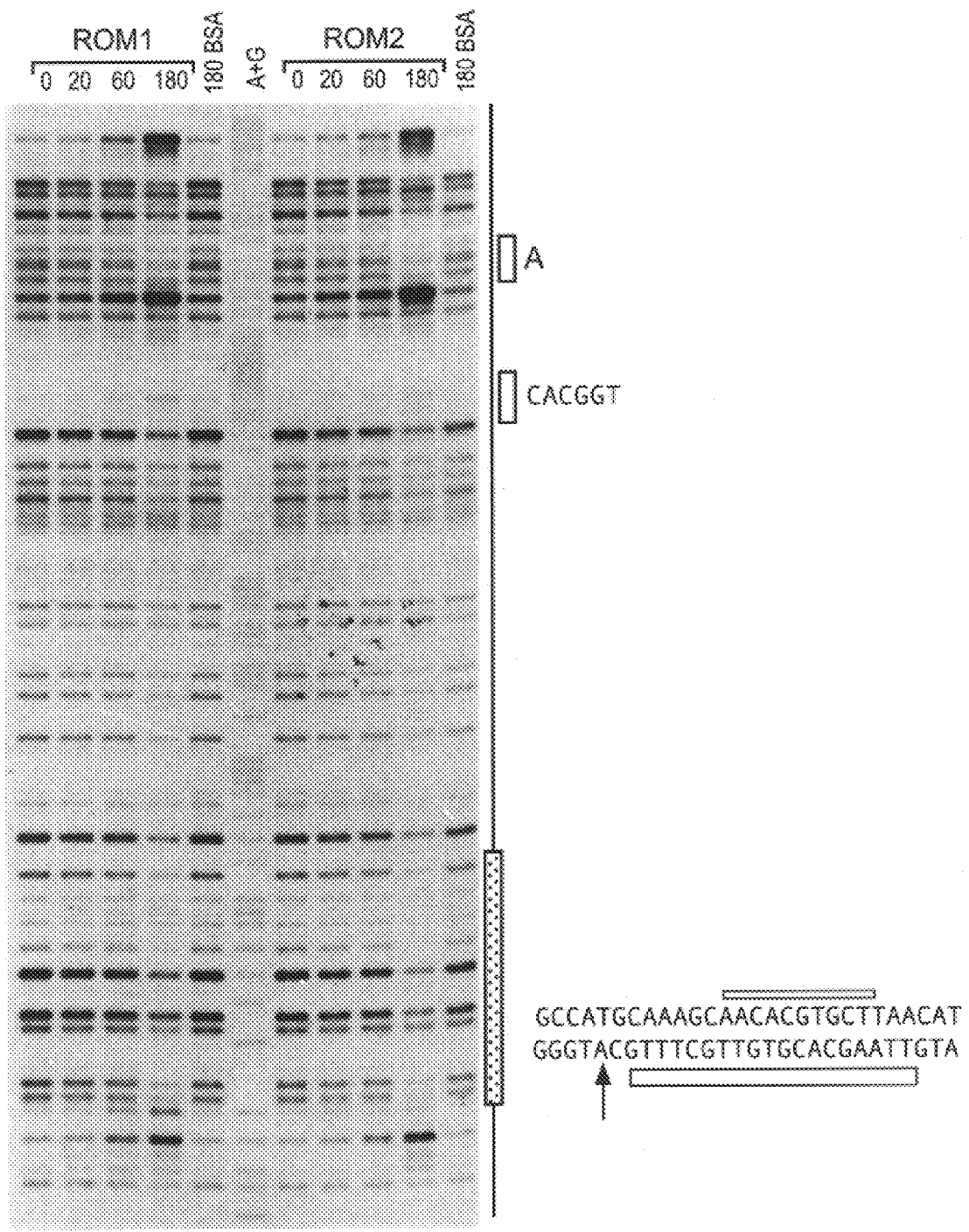

DNAseI footprinting analysis was also carried out with the PHA-L promoter. FIG. 7 shows that ROM2 and ROM1 recognize sites A, B and C corresponding to the three putative PHA-L vicilin-box motifs. Quantitative estimates of the equilibrium constants for association of ROM2 and ROM1 at each site were made using the DNAseI footprinting titration technique (Brenowitz et al.,1986). This procedure involved incubating a constant amount of the radiolabeled target DNA with increasing amounts of each protein prior to exposure to DNAseI. For each site, the fraction of occupied to vacant sites (Yapp/1-Yapp) was determined from radiometric measurements made with a Phosphorimager (Molecular Dynamics). The resulting values were plotted as a function of protein concentration (Brenowitz et al.,1986), and apparent equilibrium constants of association were calculated as the slope of the linear regression. Values obtained from this analysis are displayed on.

Table 1

[SEQ ID NOS: 19–21] Equilibrium constants for association of ROM1 and ROM2 to sites on the phytohemagglutinin (PHA-L) promoter.

| Site | Sequence | Position (bp) | ROM1<br>Ka ± S.E.$^a$(10$^9$M$^{-1}$) | ROM2<br>Ka + S.E.$^a$(10$^9$M$^{-1}$) |
|---|---|---|---|---|
| A | 5'GCC<u>ACGT</u>CAG3' | −206 | 5.0 ± 0.2 | 11 ± 2 |
| B | 5'GCC<u>ACCT</u>CAG3' | −162 | 1.0 ± 0.3 | 9 ± 3 |
| C | 5'GCC<u>ACCT</u>CAG3' | −102 | 0.70 ± 0.04 | 6.6 ± 0.1 |

$^a$Ka values were calculated by linear regression. S.E.: Standard error of the regression.

Due to uncertainties in the concentration and activities of ROM1 and ROM2 protein dimers, these estimates are only approximations of the real association constants and comparisons between the two proteins should be avoided. Nevertheless, by comparing the association constants of each protein at site A versus the other two sites it becomes clear that the absence of a symmetric, ACGT core has a more pronounced effect on ROM1 than on ROM2. From these experiments we concluded that ROM2 has a 5–10 fold greater relative affinity for asymmetric vicilin-box motifs than ROM1.

Inspection of the nucleotide sequences of over twenty storage proteins, lectin and oleosin promoters from legumes, Brassica, Arabidopsis, carrot and sunflower revealed that they all contain ROM2-like sites within 300 bp of the site for transcription initiation (Bustos, submitted). Often, these sites are paired with other ROM2 sites or with RY repeats (5'CATGCAY3'), which are also widely distributed throughout the same promoters. These arrangements suggest synergistic interactions between adjacent ROM2 dimers, or between VBP1 dimers and other nuclear proteins, such as the hypothetical RY binding protein.

It will be appreciated that the transcription factor genes of the present invention, such as ROM1 and ROM2, can be used as molecular probes to isolate equivalent genes from related legume species. Additionally, sense or anti-sense copies of the genes can be employed to enhance or reduce the expression of seed storage protein an oil-body protein in transgenic plants, altering the protein and oil composition of the seeds. Alternatively, protein or oil-body producing genes can be controlled independently with ROM1 or ROM2 proteins engineered to recognize subsets of promoter sequences specific for each type of target gene.

Insertion of the genes into plants is a relatively straightforward exercise. In particular, enhancement or diminishment of the production of the oil or protein content of a seed crop is achieved by controlling expression of the seed maturation genes using, for example, ROM1 or ROM2. The genes are inserted using vectors well known in the art for transformation of plants.

ROM1 and ROM2 are used in the construction of high yield expression cassettes as shown in FIG. 8. The first cassette system shown in FIG. 8.1 includes an expression module including a special purpose gene (SPG) driven by a Type-I-dependent promoter, and a booster module containing one or more copies of ROM2 under the control of a Ts/Type I promoter. The Ts element detects the presence of tissue specific factors and acts as a starter, initiating expression of ROM2 at the correct time of development. After a period of synthesis, ROM2 increases it own level of expression via a positive feedback mechanism and activates SPG synthesis. In this system, the levels of ROM2 protein increase until its synthesis becomes limited by the availability of cellular factors involved in transcription and translation of the ROM2 mRNA. Since excessive amounts of a transcription factor are probably undesirable, the capability for auto-regulation is provided in the system shown in FIG. 8.2. This design utilizes two different types of promoters; a Type I promoter sensitive to ROM2 and ROM1*, and a Type II promoter that responds only to ROM2. As before, the VBP1 gene is controlled by a hybrid TS/TypeI promoter. A modified version of gene ROM1 (ROM1*) and the special purpose gene (SPG) are controlled by a Type II promoter. The product of gene ROM1* differs from normal ROM1 in two ways; it lacks a functional transcription activation domain and its dimerization domain has been modified to keep it from forming heterodimers with ROM2. Consequently, the ROM1* protein is still capable of competing with ROM2 for access to the Type I promoter but is unable to activate ROM2 expression. Consequently, ROM1* functions as a competitive inhibitor of the Type I promoter. Experimental data demonstrate that the affinity of the ROM1 DNA binding domain for Type II promoters is 10–100 fold lower than that of ROM2. Consequently, the ROM1* protein should have little or no effect of SPG expression. This design limits the amount of ROM2 protein. More important, the relative affinities of ROM2 and ROM1* proteins for Type I and II promoters can be fine tuned to alter the balance of positive and negative regulation acting upon the Type I promoter and thus, increase the net amount of ROM2 protein available to activate SPG expression.

Although only preferred embodiments of the invention are specifically illustrated and described above, it will be appreciated that many modifications and variations of the present invention are possible in light of the above teachings and within the purview of the appended claims without departing from the spirit and intended scope of the invention.

What is claimed is:

1. An isolated transcription factor gene which is expressed in a recombinant maturing dicot seed and which encodes a transcription factor protein which targets a promoter of a gene encoding seed storage proteins, lectins or oil-body proteins, wherein said transcription factor gene is ROM1, ROM2 or is a gene which encodes an RNA which hybridizes to ROM1 or ROM2 under high stringency conditions.

2. The transcription factor gene of claim 1 wherein said transcription factor protein binds to 7S globulin (b-phaseolin) or lectin (PHA-L) promoters.

3. The transcription factor gene of claim 1 wherein said seed is a legume seed.

4. The transcription factor gene of claim 3 wherein said legume is soybean, (*Glycine max*), beans (*Phaseolus vulqaris*), broad beans (*Vicia faba*) or peas (*Pisum sativum*).

5. A recombinant vector comprising the transcription factor gene of claim 1, said vector being one which can transform a dicot seed crop.

6. A method for enhancing or reducing expression of seed storage protein, lectin or oil-protein genes in dicot seed crops comprising transforming a seed crop plant with the transcription factor gene of claim 1, said plant thereby expressing the transcription factor protein encoded by said transcription factor gene.

7. The method of claim 6 wherein expression of seed storage protein, lectin or oil-protein genes is enhanced.

8. The method of claim 6 wherein expression of seed storage protein, lectin or oil-protein genes is reduced.

9. A recombinant dicot seed crop plant transformed with the transcription factor gene of claim 1.

10. The recombinant dicot seed crop plant of claim 9 wherein said transcription factor protein binds to 7S globulin (b-phaseolin) or lectin (PHA-L) promoters.

11. The recombinant dicot seed crop plant of claim 9 wherein said gene is ROM 1 or ROM 2.

12. The recombinant dicot seed crop of claim 9 wherein said seed is a legume seed.

13. The recombinant dicot seed crop of claim 12 wherein said legume is soybean, (*Glycine max*), beans (*Phaseolus vulgaris*), broad beans (*Vicia faba*) or peas (*Pisum sativum*).

14. An expression cassette comprising the gene of claim 1.

15. An isolated transcription factor gene which is expressed in a recombinant maturing dicot seed and which encodes a transcription factor protein which targets a promoter of a gene encoding seed storage proteins, lectins or oil-body proteins, wherein said transcription factor gene is ROM1.

16. An isolated transcription factor gene which is expressed in a recombinant maturing dicot seed and which encodes a transcription factor protein which targets a promoter of a gene encoding seed storage proteins, lectins or oil-body proteins, wherein said transcription factor gene is ROM2.

* * * * *

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 10 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

CACACGTCAA      10

(2) INFORMATION FOR SEQ ID NO:2:

(i) SEQUENCE CHARACTERISTICS:
      (A) LENGTH: 35 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

GACTCGAGTC GACATCGATT TTTTTTTTTT TTTTT      35

```
(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

GACTCGAGTC GACATCGA                                                 18

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: DNA (genomic)

(ix) FEATURE:
        (A) NAME/KEY: Protein
        (B) LOCATION: 1
        (D) OTHER INFORMATION: /note= "Amino acid 3 wherein Xaa
            can be Q, E or L."

(xi) SEQUENCE DESCRIPTION: SEQ ID NO:4:

Arg Lys Xaa Ser Asn Arg Glu Ser Ala Arg Arg
1               5                   10

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

AGRAARSWDT CHAAYAG                                                  17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

AGRAARSWDT CHAAYCG                                                  17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO:7:

MGDGARTCHG CHAGRAG                                                17

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

MGDGARTCHG CHAGRCG                                                17

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

ATTACAATTG AGGGTTA                                                17

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CCATCAAACA CTACACTGAG                                             20

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

ACTCAGATAC CATTAGA                                                17

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

TTCACACCAG TACAGTTAAT                                             20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CCCAGTTGAG TATTTCTCAG                                              20
```

(2) INFORMATION FOR SEQ ID NO:14:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

```
GGAAGCTTAG TAACATCTGC ACTGTGG                                      27
```

(2) INFORMATION FOR SEQ ID NO:15:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
GGTCTAGACC ATCATTCTCT TCTCTCTA                                     28
```

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

```
GCCACCTCAA                                                         10
```

(2) INFORMATION FOR SEQ ID NO:17:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

```
GCGTGTCAT                                                           9
```

(2) INFORMATION FOR SEQ ID NO:18:

(i) SEQUENCE CHARACTERISTICS:

```
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

AACACGTGCT                                                            10

(2) INFORMATION FOR SEQ ID NO:19:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GCCACGTCAG                                                            10

(2) INFORMATION FOR SEQ ID NO:20:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GCCACCTCAG                                                            10

(2) INFORMATION FOR SEQ ID NO:21:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

GCCACCTCAG                                                            10

(2) INFORMATION FOR SEQ ID NO:22:

(i) SEQUENCE CHARACTERISTICS:
        (A) LENGTH: 1546 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

AATTTGTGTT TCACATTCCA ACTAGCGTGC GCTGGTACAA TCCACCGTGC CCACACCTCA      60

CCCTTCTCCT TTTCTCTTTC GAGTTTCCAA CGCAACAACA GCCACAGGAG TTGTTGAAAA     120

TAACAAACAA ACATTTACTG TTACCCTCCT ACCTTCTCAG ACGCACGCCA CAACAACCAC     180

CTTCTCAGAC ACAACACTAA CAAACGTTTC TTTGCAACAC TCTTCAGTTT CAGTTTTCCC     240

ATGATACAAT TATAGCTACA TCAAACCAAA AGCCTAGTGT CGAATTATTG ACTTCAAATT     300
```

-continued

```
TTAAATCCAC TTTGTCCCAT CCCACCTGGA CTTCCACCTC ATCCTTCTTC TCAACGCCAT      360

GAAAATAGTG TGTGTTTTCT GACAGGAATC TATTCAACTA GATCTTCTGA CCTCCATAGA      420

TATCAGCACT TGATCATAGG TCTTTTTTGT TTCTGTGGCT GAGAGGAAGT GATTCTAAAC      480

TAATCTATAT GGGGGCTGGG GAAGAGAGCA CAACAAAATC TTCCAAGTCA TCTTCATCAG      540

TTCAGGAGAC ACCAACAGTG CCTGCATATC CTGATTGGTC AAGCTCCATG CAGGCCTATT      600

ATGCTCCTGG AGCTGCTCCA CCTCCCTTTT TTGCCTCAAC TGTTGCATCC CCAACTCCCC      660

ATCCCTATTT ATGGGGAAGC CAGCATCCTT TGATGCCACC ATATGGGACT CCTGTCCCAT      720

ATCCAGCTTT ATATCCTCCT GGGAGTATCT ATGCTCATCA TCCAAGCATG GCAGTGACTC      780

CGAGTGTTGT CCAGCAAAGT ACGGAGATTG AAGGGAAGGG AACTGATGGA AAGGATCGAG      840

ACTCGTCCAA AAAATTGAAA GGAACTTCTG CAAATGCAGG TTCCAAAGCA GGAGAGAGTG      900

GAAAGGCAGG CTCAGGTTCA GGCAATGATG GCATGTCTCA AAGTGGTGAA AGTGGTTCAG      960

AGGGTTCATC GAATGCTAGT GATGAGAATA ATAACCAACA GGAATCAGCT ACAAACAAGA     1020

AGGGAAGCTT TGACCTGATG CTTGTTGATG GAGCCAATGC CCAGAACAAT TCTGGGGGTG     1080

CCATTTCTCA ATCTTCTATG CCTGGGAAGC CTGTTGTCTC AATGCCAGCA ACTAATCTTA     1140

ATATTGGAAT GGACTTATGG AATGCATCAT CCGGTGGTGG CGAAGCTGCA AAAATGAGAC     1200

ATAATCAATC TGGTGCCCCA GGAGTTGTTG CCCTTGGTGA ACAATGGATA CAAGATGAAC     1260

GTGAGCTGAA AAGACAGAAG AGAAAACAGT CAAACAGAGA CTCAGCTAGG AGGTCAAGGT     1320

TACGCAAGCA GGCTGAGTGC GAAGACTTAC AAAAGAGGGT GGAGACACTG GGAAGTGAGA     1380

ATCGAACACT CAGAGAAGAG CTTCAGAGAC TTTCCGAAGA ATGCGAGAAG CTTACATCTG     1440

AAAATAGTTC AATCAAGGAA GAATTGGAAC GGATGTGTGG GCCAGAAGCA GTTGCTAACC     1500

TTGGATGACA CAAAACATTT GAGTTCCTCA GTGTAGTGTT TGATGG                   1546
```

(2) INFORMATION FOR SEQ ID NO:23:

(i) SEQUENCE CHARACTERISTICS:
        (A) LENGTH: 515 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
Asn Leu Cys Phe Thr Phe Gln Leu Ala Cys Ala Gly Thr Ile His Arg
1               5                   10                  15

Ala His Thr Ser Pro Phe Ser Phe Ser Leu Ser Ser Phe Gln Arg Asn
            20                  25                  30

Asn Ser His Arg Ser Cys Xaa Lys Xaa Gln Thr Asn Ile Tyr Cys Tyr
        35                  40                  45

Pro Pro Thr Phe Ser Asp Ala Arg His Asn Asn His Leu Leu Arg His
    50                  55                  60

Asn Thr Asn Lys Arg Phe Phe Ala Thr Leu Phe Ser Phe Ser Phe Pro
65                  70                  75                  80

Met Ile Gln Leu Xaa Leu His Gln Thr Lys Ser Leu Val Ser Asn Tyr
                85                  90                  95

Xaa Leu Gln Ile Leu Asn Pro Leu Cys Pro Ile Pro Gly Leu Pro
            100                 105                 110

Pro His Pro Ser Ser Gln Arg His Glu Asn Ser Val Cys Phe Leu Thr
        115                 120                 125
```

```
Gly Ile Tyr Ser Thr Arg Ser Ser Asp Leu His Arg Tyr Gln His Leu
    130                 135                 140

Ile Ile Gly Leu Phe Cys Phe Cys Gly Xaa Glu Val Ile Leu Asn
145                 150                 155                 160

Xaa Ser Ile Trp Gly Leu Gly Lys Arg Ala Gln Gln Asn Leu Pro Ser
                165                 170                 175

His Leu His Gln Phe Arg Arg His Gln Gln Cys Leu His Ile Leu Ile
            180                 185                 190

Gly Gln Ala Pro Cys Arg Pro Ile Met Leu Leu Glu Leu Leu His Leu
        195                 200                 205

Pro Phe Leu Pro Gln Leu Leu His Pro Gln Leu Pro Ile Pro Ile Tyr
    210                 215                 220

Gly Glu Ala Ser Ile Leu Xaa Cys His His Met Gly Leu Leu Ser His
225                 230                 235                 240

Ile Gln Leu Tyr Ile Leu Leu Gly Val Ser Met Leu Ile Ile Gln Ala
                245                 250                 255

Trp Gln Xaa Leu Arg Val Leu Ser Ser Lys Val Arg Arg Leu Lys Gly
            260                 265                 270

Arg Glu Leu Met Glu Arg Ile Glu Thr Arg Pro Lys Asn Xaa Lys Glu
        275                 280                 285

Leu Leu Gln Met Gln Val Pro Lys Gln Glu Arg Val Glu Arg Gln Ala
    290                 295                 300

Gln Val Gln Ala Met Met Ala Cys Leu Lys Val Val Lys Val Val Gln
305                 310                 315                 320

Arg Val His Arg Met Leu Val Met Arg Ile Ile Thr Asn Arg Asn Gln
                325                 330                 335

Leu Gln Thr Arg Arg Glu Ala Leu Thr Xaa Cys Leu Leu Met Glu Pro
            340                 345                 350

Met Pro Arg Thr Ile Leu Gly Val Pro Phe Leu Asn Leu Leu Cys Leu
        355                 360                 365

Gly Ser Leu Leu Ser Gln Cys Gln Gln Leu Ile Leu Ile Leu Glu Trp
    370                 375                 380

Thr Tyr Gly Met His His Pro Val Val Ala Lys Leu Gln Lys Xaa Asp
385                 390                 395                 400

Ile Ile Asn Leu Val Pro Gln Glu Leu Leu Pro Leu Val Asn Asn Gly
                405                 410                 415

Tyr Lys Met Asn Val Ser Xaa Lys Asp Arg Arg Glu Asn Ser Gln Thr
            420                 425                 430

Glu Ser Gln Leu Gly Gly Gln Gly Tyr Ala Ser Arg Leu Ser Ala Lys
        435                 440                 445

Thr Tyr Lys Arg Gly Trp Arg His Trp Glu Val Arg Ile Glu His Ser
    450                 455                 460

Glu Lys Ser Phe Arg Asp Phe Pro Lys Asn Ala Arg Ser Leu His Leu
465                 470                 475                 480

Lys Ile Val Gln Ser Arg Lys Asn Trp Asn Gly Cys Val Gly Gln Lys
                485                 490                 495

Gln Leu Leu Thr Leu Asp Asp Thr Lys His Leu Ser Ser Ser Val Xaa
            500                 505                 510

Cys Leu Met
        515

(2) INFORMATION FOR SEQ ID NO:24:

(i) SEQUENCE CHARACTERISTICS:
```

(A) LENGTH: 515 amino acids
(B) TYPE: amino acid
(C) STRANDEDNESS: single
(D) TOPOLOGY: linear (ii) MOLECULE TYPE: DNA (genomic)

(xi) SEQUENCE DESCRIPTION: SEQ ID NO:24:

```
Ile Cys Val Ser His Ser Asn Xaa Arg Ala Leu Val Gln Ser Thr Val
1               5                   10                  15

Pro Thr Pro His Pro Ser Pro Phe Leu Phe Arg Val Ser Asn Ala Thr
                20                  25                  30

Thr Ala Thr Gly Val Val Glu Asn Asn Lys Gln Thr Phe Thr Val Thr
            35                  40                  45

Leu Leu Pro Ser Gln Thr His Ala Thr Thr Thr Phe Ser Asp Thr
    50                  55                  60

Thr Leu Thr Asn Val Ser Leu Gln His Ser Ser Val Ser Val Phe Pro
65                  70                  75                  80

Xaa Tyr Asn Tyr Ser Tyr Ile Lys Pro Lys Ala Xaa Cys Arg Ile Ile
                85                  90                  95

Asp Phe Lys Phe Xaa Ile His Phe Val Pro Ser His Leu Asp Phe His
                100                 105                 110

Leu Ile Leu Leu Leu Asn Ala Met Lys Ile Val Cys Val Phe Xaa Gln
            115                 120                 125

Glu Ser Ile Gln Leu Asp Leu Leu Thr Ser Ile Asp Ile Ser Thr Xaa
        130                 135                 140

Ser Xaa Val Phe Phe Val Ser Val Ala Glu Arg Lys Xaa Phe Xaa Thr
145                 150                 155                 160

Asn Leu Tyr Gly Gly Trp Gly Arg Glu His Asn Lys Ile Phe Gln Val
                165                 170                 175

Ile Phe Ile Ser Ser Gly Asp Thr Asn Ser Ala Cys Ile Ser Xaa Leu
                180                 185                 190

Val Lys Leu His Ala Gly Leu Leu Cys Ser Trp Ser Cys Ser Thr Ser
            195                 200                 205

Leu Phe Cys Leu Asn Cys Cys Ile Pro Asn Ser Pro Ser Leu Phe Met
    210                 215                 220

Gly Lys Pro Ala Ser Phe Asp Ala Thr Ile Trp Asp Ser Cys Pro Ile
225                 230                 235                 240

Ser Ser Phe Ile Ser Ser Trp Glu Tyr Leu Cys Ser Ser Ser Lys His
                245                 250                 255

Gly Ser Asp Ser Glu Cys Cys Pro Ala Lys Tyr Gly Asp Xaa Arg Glu
                260                 265                 270

Gly Asn Xaa Trp Lys Gly Ser Arg Leu Val Gln Lys Ile Glu Arg Asn
            275                 280                 285

Phe Cys Lys Cys Arg Phe Gln Ser Arg Arg Glu Trp Lys Gly Arg Leu
    290                 295                 300

Arg Phe Arg Gln Xaa Trp His Val Ser Lys Trp Xaa Lys Trp Phe Arg
305                 310                 315                 320

Gly Phe Ile Glu Cys Xaa Xaa Xaa Glu Xaa Xaa Pro Thr Gly Ile Ser
                325                 330                 335

Tyr Lys Gln Glu Gly Lys Leu Xaa Pro Asp Ala Cys Xaa Trp Ser Gln
            340                 345                 350

Cys Pro Glu Gln Phe Trp Gly Cys His Phe Ser Ile Phe Tyr Ala Trp
        355                 360                 365

Glu Ala Cys Cys Leu Asn Ala Ser Asn Xaa Ser Xaa Tyr Trp Asn Gly
```

-continued

```
            370                 375                 380
Leu Met Glu Cys Ile Ile Arg Trp Trp Arg Ser Cys Lys Asn Glu Thr
385                 390                 395                 400

Xaa Ser Ile Trp Cys Pro Arg Ser Cys Cys Pro Trp Xaa Thr Met Asp
                    405                 410                 415

Thr Arg Xaa Thr Xaa Ala Glu Lys Thr Glu Glu Lys Thr Val Lys Gln
            420                 425                 430

Arg Val Ser Glu Xaa Val Lys Val Thr Gln Ala Gly Xaa Val Arg Arg
            435                 440                 445

Leu Thr Lys Glu Gly Gly Asp Thr Gly Lys Xaa Glu Ser Asn Thr Gln
            450                 455                 460

Arg Arg Ala Ser Glu Thr Phe Arg Arg Met Arg Glu Ala Tyr Ile Xaa
465                 470                 475                 480

Lys Xaa Phe Asn Gln Gly Arg Ile Gly Thr Asp Val Trp Ala Arg Ser
            485                 490                 495

Ser Cys Xaa Pro Trp Met Thr Gln Asn Ile Xaa Val Pro Gln Cys Ser
            500                 505                 510

Val Xaa Trp
    515
```

(2) INFORMATION FOR SEQ ID NO:25:

(i) SEQUENCE CHARACTERISTICS:
      (A) LENGTH: 514 amino acids
      (B) TYPE: amino acid
      (C) STRANDEDNESS: single
      (D) TOPOLOGY: linear (ii) MOLECULE TYPE: DNA (genomic)

(xi) SEQUENCE DESCRIPTION: SEQ ID NO:25:

```
Phe Val Phe His Ile Pro Thr Ser Val Arg Trp Tyr Asn Pro Pro Cys
1               5                   10                  15

Pro His Leu Thr Leu Leu Leu Phe Ser Phe Glu Phe Pro Thr Gln Gln
                20                  25                  30

Gln Pro Gln Glu Leu Leu Lys Ile Thr Asn Lys His Leu Leu Leu Pro
            35                  40                  45

Ser Tyr Leu Leu Arg Arg Thr Pro Gln Gln Pro Ser Gln Thr Gln
50                  55                  60

His Xaa Gln Thr Phe Leu Cys Asn Thr Leu Gln Phe Gln Phe Ser His
65                  70                  75                  80

Asp Thr Ile Ile Ala Thr Ser Asn Gln Lys Pro Ser Val Glu Leu Leu
                85                  90                  95

Thr Ser Asn Phe Lys Ser Thr Leu Ser His Pro Thr Trp Thr Ser Thr
                100                 105                 110

Ser Ser Phe Phe Ser Thr Pro Xaa Lys Xaa Cys Val Phe Ser Asp Arg
            115                 120                 125

Asn Leu Phe Asn Xaa Ile Phe Xaa Pro Pro Xaa Ile Ser Ala Leu Asp
            130                 135                 140

His Arg Ser Phe Leu Phe Leu Trp Leu Arg Gly Ser Asp Ser Lys Leu
145                 150                 155                 160

Ile Tyr Met Gly Ala Gly Glu Glu Ser Thr Thr Lys Ser Ser Lys Ser
                165                 170                 175

Ser Ser Ser Val Gln Glu Thr Pro Thr Val Pro Ala Tyr Pro Asp Trp
            180                 185                 190

Ser Ser Ser Met Gln Ala Tyr Tyr Ala Pro Gly Ala Ala Pro Pro Pro
```

```
              195                 200                 205
    Phe Phe Ala Ser Thr Val Ala Ser Pro Thr Pro His Pro Tyr Leu Trp
        210                 215                 220

Gly Ser Gln His Pro Leu Met Pro Pro Tyr Gly Thr Pro Val Pro Tyr
    225                 230                 235                 240

Pro Ala Leu Tyr Pro Pro Gly Ser Ile Tyr Ala His His Pro Ser Met
                    245                 250                 255

Ala Val Thr Pro Ser Val Val Gln Gln Ser Thr Glu Ile Glu Gly Lys
                260                 265                 270

Gly Thr Asp Gly Lys Asp Arg Asp Ser Ser Lys Lys Leu Lys Gly Thr
                275                 280                 285

Ser Ala Asn Ala Gly Ser Lys Ala Gly Glu Ser Gly Lys Ala Gly Ser
                290                 295                 300

Gly Ser Gly Asn Asp Gly Met Ser Gln Ser Gly Glu Ser Gly Ser Glu
    305                 310                 315                 320

Gly Ser Ser Asn Ala Ser Asp Glu Asn Asn Asn Gln Gln Glu Ser Ala
                    325                 330                 335

Thr Asn Lys Lys Gly Ser Phe Asp Leu Met Leu Val Asp Gly Ala Asn
                340                 345                 350

Ala Gln Asn Asn Ser Gly Gly Ala Ile Ser Gln Ser Ser Met Pro Gly
                355                 360                 365

Lys Pro Val Val Ser Met Pro Ala Thr Asn Leu Asn Ile Gly Met Asp
    370                 375                 380

Leu Trp Asn Ala Ser Ser Gly Gly Gly Glu Ala Ala Lys Met Arg His
    385                 390                 395                 400

Asn Gln Ser Gly Ala Pro Gly Val Val Ala Leu Gly Glu Gln Trp Ile
                    405                 410                 415

Gln Asp Glu Arg Glu Leu Lys Arg Gln Lys Arg Lys Gln Ser Asn Arg
                420                 425                 430

Glu Ser Ala Arg Arg Ser Arg Leu Arg Lys Gln Ala Glu Cys Glu Asp
                435                 440                 445

Leu Gln Lys Arg Val Glu Thr Leu Gly Ser Glu Asn Arg Thr Leu Arg
                450                 455                 460

Glu Glu Leu Gln Arg Leu Ser Glu Glu Cys Glu Lys Leu Thr Ser Glu
    465                 470                 475                 480

Asn Ser Ser Ile Lys Glu Glu Leu Glu Arg Met Cys Gly Pro Glu Ala
                    485                 490                 495

Val Ala Asn Leu Gly Xaa His Lys Thr Phe Glu Phe Leu Ser Val Val
                500                 505                 510

Phe Asp (2) INFORMATION FOR SEQ ID NO:26:

(i) SEQUENCE CHARACTERISTICS:
        (A) LENGTH: 1657 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:26:

TTGGGTTCAT CTGAATAACT TGTTGGGACA TATTTGTTTG GTGCTTTTCT TTTGGTGATT      60

GCCTCATGGG AAACAGTGAG GAAGGGAAAT CTGTTAAAAC TGGAAGTCCT TCTTCACCAG     120

CTACAACTGA ACAGACCAAT CAGACAAACC AGCCTAACTT TCATGTCTAT CCTGATTGGG    180
```

```
CTGCCATGCA GTATTATGGG CCGAGAGTCA ACATTCCTCC ATACTTCAAC TCGGCTGTGG      240

CTTCTGGTCA TGCTCCACAC CCATACATGT GGGGTCCACC ACAGCCTATG ATGCCACCTT      300

ATGGGCCACC ATATGCAGCA TTTTATTCTC CTGGAGGGGT TTATACTCAC CCTGCAGTTG      360

CTATTGGGCC ACATTCACAC GGTCAAGGAG TTCCATCCCC ACCTGCTGCT GGGACTCCTT      420

CAAGTGTAGA TTCACCAACA AAATTATCTG GAAATACTGA TCAAGGGTTA ATGAAAAAAT      480

TGAAAGGGTT TGATGGGCTT GCAATGTCAA TAGGCAATTG CAATGCTGAG AGTGCGGAGC      540

TTGGAGCTGA AAACAGGCTG TCGCAGAGTG TGGATACTGA GGGTTCTAGC GATGGAAGTG      600

ATGGCAACAC TGCAGGGGCT AATCAAACAA AAATGAAAAG AAGCCGAGAG GAAACATCAA      660

CCACTGATGG AGAAGGGAAA ACTGAGACAC AAGATGGGCC AGTTTCCAAA GAGACTACAT      720

CTTCGAAAAT GGTTATGTCT GCTACACCAG CTAGTGTTGC AGGAAAGTTA GTTGGTCCTG      780

TAATTTCTTC AGGTATGACC ACAGCACTGG AGCTTAGGAA ACCTTTGACT GTTCATTCTA      840

AGGAAAATCC CACGAGTGCC CCACAACCTT GTGCAGCTGT GCCTCCTGAA GCTTGGTTAC      900

AGAATGAGCG TGAGCTGAAA CGGGAGAGGA GGAAACAATC TAACCGTGAA TCTGCTAGAA      960

GGTCCAGGCT GAGGAAGCAG GCCGAGACTG AAGAATTGGC ACGAAAAGTT GAGATGTTAA     1020

CTGCTGAAAA TGTGTCACTG AAGTCAGAAA TAACTCAATT GACTGAAGGT TCTGAGCAGA     1080

TGAGGATGGA AAATTCTGCA TTGAGGGAAA AACTGAGAAA TACTCAACTG GGACAAAGGG     1140

AAGAGATAAT TTTGGACAGC ATTGACAGCA AGAGGTCTAC ACCTGTAAGT ACTGAAAATT     1200

TGCTATCAAG AGTTAATAAT TCCAGTTCTA ATGATAGAAG TGCAGAGAAT GAGAGTGATT     1260

TCTGTGAGAA CAAACCAAAT TCTGGTGCAA AGCTGCATCA ACTACTGGAT ACAAATCCTA     1320

GAGCTGATGC TGTTGCTGCT GGGTGAAACC AGTAATTGCA CTGGCTTATT ATGTAACTTT     1380

GGCATATTAC AAGTCCAAAA TTACAGCTTG GTGCTAACAG TTTTCAGAGG ATGGATCAGC     1440

TGAGTTTTAC AACCTAAATC CATCTATAGA CCAGGACTAA TTCTTTGCTT GTCAGTTTCT     1500

TAGGACATAA ACTCTGTATT TTATTAGAAT TGACAGAAAT GGATGACAAC TTTAAAGAAG     1560

TTTGTAAATG TAAGAGTATT AGGGATCTAG TTTAGATTTT AAGATAGGGT TGTCAACCTC     1620

TGTATAATTG GTTGTGCATT AACTGTACTG GTGTGAA                              1657
```

(2) INFORMATION FOR SEQ ID NO:27:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:27:

```
Leu Gly Ser Ser Glu Xaa Leu Val Gly Thr Tyr Leu Phe Gly Ala Phe
  1               5                  10                  15

Leu Leu Val Ile Ala Ser Trp Glu Thr Val Arg Lys Gly Asn Leu Leu
             20                  25                  30

Lys Leu Glu Val Leu Leu His Gln Leu Gln Leu Asn Arg Pro Ile Arg
         35                  40                  45

Gln Thr Ser Leu Thr Phe Met Ser Ile Leu Ile Gly Leu Pro Cys Ser
     50                  55                  60

Ile Met Gly Arg Glu Ser Thr Phe Leu His Thr Ser Thr Arg Leu Trp
 65                  70                  75                  80
```

-continued

```
Leu Leu Val Met Leu His Thr His Thr Cys Gly Val His His Ser Leu
                85                  90                  95

Xaa Cys His Leu Met Gly His His Met Gln His Phe Ile Leu Leu Glu
            100                 105                 110

Gly Phe Ile Leu Thr Leu Gln Leu Leu Gly His Ile His Thr Val
        115                 120                 125

Lys Glu Phe His Pro His Leu Leu Gly Leu Leu Gln Val Xaa Ile
130                 135                 140

His Gln Gln Asn Tyr Leu Glu Ile Leu Ile Lys Gly Xaa Xaa Lys Asn
145                 150                 155                 160

Xaa Lys Gly Leu Met Gly Leu Gln Cys Gln Xaa Ala Ile Ala Met Leu
                165                 170                 175

Arg Val Arg Ser Leu Glu Leu Lys Thr Gly Cys Arg Arg Val Trp Ile
            180                 185                 190

Leu Arg Val Leu Ala Met Glu Val Met Ala Thr Leu Gln Gly Leu Ile
        195                 200                 205

Lys Gln Lys Xaa Lys Glu Ala Glu Arg Lys His Gln Pro Leu Met Glu
    210                 215                 220

Lys Gly Lys Leu Arg His Lys Met Gly Gln Phe Pro Lys Arg Leu His
225                 230                 235                 240

Leu Arg Lys Trp Leu Cys Leu Leu His Gln Leu Val Leu Gln Glu Ser
                245                 250                 255

Xaa Leu Val Leu Xaa Phe Leu Gln Val Xaa Pro Gln His Trp Ser Leu
            260                 265                 270

Gly Asn Leu Xaa Leu Phe Ile Leu Arg Lys Ile Pro Arg Val Pro His
        275                 280                 285

Asn Leu Val Gln Leu Cys Leu Leu Lys Leu Gly Tyr Arg Met Ser Val
    290                 295                 300

Ser Xaa Asn Gly Arg Gly Gly Asn Asn Leu Thr Val Asn Leu Leu Glu
305                 310                 315                 320

Gly Pro Gly Xaa Gly Ser Arg Pro Arg Leu Lys Asn Trp His Glu Lys
                325                 330                 335

Leu Arg Cys Xaa Leu Leu Lys Met Cys His Xaa Ser Gln Lys Xaa Leu
            340                 345                 350

Asn Xaa Leu Lys Val Leu Ser Arg Xaa Gly Trp Lys Ile Leu His Xaa
        355                 360                 365

Gly Lys Asn Xaa Glu Ile Leu Asn Trp Asp Lys Gly Lys Arg Xaa Phe
370                 375                 380

Trp Thr Ala Leu Thr Ala Arg Gly Leu His Leu Xaa Val Leu Lys Ile
385                 390                 395                 400

Cys Tyr Gln Glu Leu Ile Ile Pro Val Leu Met Ile Glu Val Gln Arg
                405                 410                 415

Met Arg Val Ile Ser Val Arg Thr Asn Gln Ile Leu Val Gln Ser Cys
            420                 425                 430

Ile Asn Tyr Trp Ile Gln Ile Leu Glu Leu Met Leu Leu Leu Leu Gly
        435                 440                 445

Glu Thr Ser Asn Cys Thr Gly Leu Leu Cys Asn Phe Gly Ile Leu Gln
    450                 455                 460

Val Gln Asn Tyr Ser Leu Val Leu Thr Val Phe Arg Gly Trp Ile Ser
465                 470                 475                 480

Xaa Val Leu Gln Pro Lys Ser Ile Tyr Arg Pro Gly Leu Ile Leu Cys
                485                 490                 495

Leu Ser Val Ser Xaa Asp Ile Asn Ser Val Phe Tyr Xaa Asn Xaa Gln
```

```
            500             505             510
Lys Trp Met Thr Thr Leu Lys Lys Phe Val Asn Val Arg Val Leu Gly
            515             520             525

Ile Xaa Phe Arg Phe Xaa Asp Arg Val Val Asn Leu Cys Ile Ile Gly
            530             535             540

Cys Ala Leu Thr Val Leu Val Xaa
545             550

(2) INFORMATION FOR SEQ ID NO:28:

(i) SEQUENCE CHARACTERISTICS:
        (A) LENGTH: 552 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:28:

Trp Val His Leu Asn Asn Leu Leu Gly His Ile Cys Leu Val Leu Phe
1               5               10              15

Phe Trp Xaa Leu Pro His Gly Lys Gln Xaa Gly Arg Glu Ile Cys Xaa
            20              25              30

Asn Trp Lys Ser Phe Phe Thr Ser Tyr Asn Xaa Thr Asp Gln Ser Asp
            35              40              45

Lys Pro Ala Xaa Leu Ser Cys Leu Ser Xaa Leu Gly Cys His Ala Val
            50              55              60

Leu Trp Ala Glu Ser Gln His Ser Ser Ile Leu Gln Leu Gly Cys Gly
65              70              75              80

Phe Trp Ser Cys Ser Thr Pro Ile His Val Gly Ser Thr Thr Ala Tyr
                85              90              95

Asp Ala Thr Leu Trp Ala Thr Ile Cys Ser Ile Leu Phe Ser Trp Arg
            100             105             110

Gly Leu Tyr Ser Pro Cys Ser Cys Tyr Trp Ala Thr Phe Thr Arg Ser
            115             120             125

Arg Ser Ser Ile Pro Thr Cys Cys Trp Asp Ser Phe Lys Cys Arg Phe
130             135             140

Thr Asn Lys Ile Ile Trp Lys Tyr Xaa Ser Arg Val Asn Glu Lys Ile
145             150             155             160

Glu Arg Val Xaa Trp Ala Cys Asn Val Asn Arg Gln Leu Gln Cys Xaa
            165             170             175

Glu Cys Gly Ala Trp Ser Xaa Lys Gln Ala Val Ala Glu Cys Gly Tyr
            180             185             190

Xaa Gly Phe Xaa Arg Trp Lys Xaa Trp Gln His Cys Arg Gly Xaa Ser
            195             200             205

Asn Lys Asn Glu Lys Pro Arg Gly Asn Ile Asn His Xaa Trp Arg
            210             215             220

Arg Glu Asn Xaa Asp Thr Arg Trp Ala Ser Phe Gln Arg Asp Tyr Ile
225             230             235             240

Phe Glu Asn Gly Tyr Val Cys Tyr Thr Ser Xaa Cys Cys Arg Lys Val
            245             250             255

Ser Trp Ser Cys Asn Phe Phe Arg Tyr Asp His Ser Thr Gly Ala Xaa
            260             265             270

Glu Thr Phe Asp Cys Ser Phe Xaa Gly Lys Ser His Glu Cys Pro Thr
            275             280             285

Thr Leu Cys Ser Cys Ala Ser Xaa Ser Leu Val Thr Glu Xaa Ala Xaa
```

-continued

```
            290                 295                 300
Ala Glu Thr Gly Glu Glu Glu Thr Ile Xaa Pro Xaa Ile Cys Xaa Lys
305                 310                 315                 320

Val Gln Ala Glu Glu Ala Gly Arg Asp Xaa Arg Ile Gly Thr Lys Ser
                325                 330                 335

Xaa Asp Val Asn Cys Xaa Lys Cys Val Thr Glu Val Arg Asn Asn Ser
            340                 345                 350

Ile Asp Xaa Arg Phe Xaa Ala Asp Glu Asp Gly Lys Phe Cys Ile Glu
                355                 360                 365

Gly Lys Thr Glu Lys Tyr Ser Thr Gly Thr Lys Gly Arg Asp Asn Phe
            370                 375                 380

Gly Gln His Xaa Gln Gln Glu Val Tyr Thr Cys Lys Tyr Xaa Lys Phe
385                 390                 395                 400

Ala Ile Lys Ser Xaa Xaa Phe Gln Phe Xaa Xaa Xaa Lys Cys Arg Glu
                405                 410                 415

Xaa Glu Xaa Phe Leu Xaa Glu Gln Thr Lys Phe Trp Cys Lys Ala Ala
            420                 425                 430

Ser Thr Thr Gly Tyr Lys Ser Xaa Ser Xaa Cys Cys Cys Cys Trp Val
                435                 440                 445

Lys Pro Val Ile Ala Leu Ala Tyr Tyr Val Thr Leu Ala Tyr Tyr Lys
            450                 455                 460

Ser Lys Ile Thr Ala Trp Cys Xaa Gln Phe Ser Glu Asp Gly Ser Ala
465                 470                 475                 480

Glu Phe Tyr Asn Leu Asn Pro Ser Ile Asp Gln Asp Xaa Phe Phe Ala
                485                 490                 495

Cys Gln Phe Leu Arg Thr Xaa Thr Leu Tyr Phe Ile Arg Ile Asp Arg
            500                 505                 510

Asn Gly Xaa Gln Leu Xaa Arg Ser Leu Xaa Met Xaa Glu Tyr Xaa Gly
            515                 520                 525

Ser Ser Leu Asp Phe Lys Ile Gly Leu Ser Thr Ser Val Xaa Leu Val
            530                 535                 540

Val His Xaa Leu Tyr Trp Cys Glu
545                 550

(2) INFORMATION FOR SEQ ID NO:29:

(i) SEQUENCE CHARACTERISTICS:
        (A) LENGTH: 551 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

Gly Phe Ile Xaa Ile Thr Cys Trp Asp Ile Phe Val Trp Cys Phe Ser
1               5                   10                  15

Phe Gly Asp Cys Leu Met Gly Asn Ser Glu Glu Gly Lys Ser Val Lys
                20                  25                  30

Thr Gly Ser Pro Ser Ser Pro Ala Thr Thr Glu Gln Thr Asn Gln Thr
            35                  40                  45

Asn Gln Pro Asn Phe His Val Tyr Pro Asp Trp Ala Ala Met Gln Tyr
        50                  55                  60

Tyr Gly Pro Arg Val Asn Ile Pro Pro Tyr Phe Asn Ser Ala Val Ala
65              70                  75                  80

Ser Gly His Ala Pro His Pro Tyr Met Trp Gly Pro Pro Gln Pro Met
```

-continued

```
                85                  90                  95
Met Pro Pro Tyr Gly Pro Pro Tyr Ala Ala Phe Tyr Ser Pro Gly Gly
                    100                 105                 110

Val Tyr Thr His Pro Ala Val Ala Ile Gly Pro His Ser His Gly Gln
                115                 120                 125

Gly Val Pro Ser Pro Pro Ala Ala Gly Thr Pro Ser Ser Val Asp Ser
            130                 135                 140

Pro Thr Lys Leu Ser Gly Asn Thr Asp Gln Gly Leu Met Lys Lys Leu
145                 150                 155                 160

Lys Gly Phe Asp Gly Leu Ala Met Ser Ile Gly Asn Cys Asn Ala Glu
                165                 170                 175

Ser Ala Glu Leu Gly Ala Glu Asn Arg Leu Ser Gln Ser Val Asp Thr
            180                 185                 190

Glu Gly Ser Ser Asp Gly Ser Asp Gly Asn Thr Ala Gly Ala Asn Gln
                195                 200                 205

Thr Lys Met Lys Arg Ser Arg Glu Glu Thr Ser Thr Thr Asp Gly Glu
        210                 215                 220

Gly Lys Thr Glu Thr Gln Asp Gly Pro Val Ser Lys Glu Thr Thr Ser
225                 230                 235                 240

Ser Lys Met Val Met Ser Ala Thr Pro Ala Ser Val Ala Gly Lys Leu
                245                 250                 255

Val Gly Pro Val Ile Ser Ser Gly Met Thr Thr Ala Leu Glu Leu Arg
            260                 265                 270

Lys Pro Leu Thr Val His Ser Lys Glu Asn Pro Thr Ser Ala Pro Gln
                275                 280                 285

Pro Cys Ala Ala Val Pro Pro Glu Ala Trp Leu Gln Asn Glu Arg Glu
        290                 295                 300

Leu Lys Arg Glu Arg Arg Lys Gln Ser Asn Arg Glu Ser Ala Arg Arg
305                 310                 315                 320

Ser Arg Leu Arg Lys Gln Ala Glu Thr Glu Glu Leu Ala Arg Lys Val
                325                 330                 335

Glu Met Leu Thr Ala Glu Asn Val Ser Leu Lys Ser Glu Ile Thr Gln
            340                 345                 350

Leu Thr Glu Gly Ser Glu Gln Met Arg Met Glu Asn Ser Ala Leu Arg
        355                 360                 365

Glu Lys Leu Arg Asn Thr Gln Leu Gly Gln Arg Glu Glu Ile Ile Leu
370                 375                 380

Asp Ser Ile Asp Ser Lys Arg Ser Thr Pro Val Ser Thr Glu Asn Leu
385                 390                 395                 400

Leu Ser Arg Val Asn Asn Ser Ser Asn Asp Arg Ser Ala Glu Asn
                405                 410                 415

Glu Ser Asp Phe Cys Glu Asn Lys Pro Asn Ser Gly Ala Lys Leu His
            420                 425                 430

Gln Leu Leu Asp Thr Asn Pro Arg Ala Asp Ala Val Ala Ala Gly Xaa
        435                 440                 445

Asn Gln Xaa Leu His Trp Leu Ile Met Xaa Leu Trp His Ile Thr Ser
            450                 455                 460

Pro Lys Leu Gln Leu Gly Ala Asn Ser Phe Gln Arg Met Asp Gln Leu
465                 470                 475                 480

Ser Phe Thr Thr Xaa Ile His Leu Xaa Thr Arg Thr Asn Ser Leu Leu
                485                 490                 495

Val Ser Phe Leu Gly His Lys Leu Cys Ile Leu Leu Glu Leu Thr Glu
            500                 505                 510
```

```
Met Asp Asp Asn Phe Lys Glu Val Cys Lys Cys Lys Ser Ile Arg Asp
            515                 520                 525

Leu Val Xaa Ile Leu Arg Xaa Gly Cys Gln Pro Leu Tyr Asn Trp Leu
            530                 535                 540

Cys Ile Asn Cys Thr Gly Val
545                 550

(2) INFORMATION FOR SEQ ID NO:30:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

Asp Pro Ala Ala Leu Lys Arg Ala Arg Asn Thr Glu Ala Ala Arg Arg
1               5                   10                  15

Ser Arg Ala Arg Lys Leu Gln Arg Met Gln Lys Leu
            20                  25

(2) INFORMATION FOR SEQ ID NO:31:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

Asp Glu Arg Glu Leu Lys Arg Gln Lys Arg Lys Gln Ser Asn Arg Glu
1               5                   10                  15

Ser Ala Arg Arg Ser Arg Leu Arg Lys Gln Ala Glu Cys Glu Asp Leu
            20                  25                  30

Gln Lys Arg Val Glu Thr Leu Gly Ser Glu Asn Arg Thr
            35                  40                  45

(2) INFORMATION FOR SEQ ID NO:32:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

Asn Glu Arg Glu Leu Lys Arg Gln Arg Arg Lys Gln Ser Asn Arg Glu
1               5                   10                  15

Ser Ala Arg Ser Arg Leu Arg Lys Gln Ala Glu Thr Glu Glu Leu
            20                  25                  30

Ala Arg Lys Val Glu Met Leu Thr Ala Glu Asn Val Ser
            35                  40                  45
```